(12) United States Patent
Kikawa et al.

(10) Patent No.: US 8,096,658 B2
(45) Date of Patent: Jan. 17, 2012

(54) FUNDUS OCULI OBSERVATION DEVICE AND PROGRAM FOR CONTROLLING THE SAME

(75) Inventors: Tsutomu Kikawa, Tokyo (JP); Hiroyuki Aoki, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 107 days.

(21) Appl. No.: 12/600,865

(22) PCT Filed: Apr. 8, 2008

(86) PCT No.: PCT/JP2008/000905
§ 371 (c)(1),
(2), (4) Date: Nov. 19, 2009

(87) PCT Pub. No.: WO2008/142823
PCT Pub. Date: Nov. 27, 2008

(65) Prior Publication Data
US 2010/0149489 A1   Jun. 17, 2010

(30) Foreign Application Priority Data

May 23, 2007 (JP) ................................ 2007-136329

(51) Int. Cl.
*A61B 3/14* (2006.01)
*A61B 3/10* (2006.01)
(52) U.S. Cl. ......... 351/206; 351/205; 351/209; 351/221
(58) Field of Classification Search ........... 351/200–246
See application file for complete search history.

(56) References Cited

U.S. PATENT DOCUMENTS 5,975,697 A * 11/1999 Podoleanu et al. ........... 351/206
7,566,128 B2 * 7/2009 Tsukada et al. ............... 351/205

FOREIGN PATENT DOCUMENTS

| EP | 1775545 A2 | 4/2007 |
|---|---|---|
| JP | 11-325849 A | 11/1999 |
| JP | 2001-275979 A | 10/2001 |
| JP | 2002-139421 A | 5/2002 |
| JP | 2002-143088 A | 5/2002 |
| JP | 2003-000543 A | 1/2003 |
| JP | 2006-023476 A | 1/2006 |
| JP | 2007-117714 A | 5/2007 |

OTHER PUBLICATIONS

International Search Report dated May 13, 2008, issued on PCT/JP2008/000905.

* cited by examiner

*Primary Examiner* — Mohammed Hasan
(74) *Attorney, Agent, or Firm* — Edwards Wildman Palmer LLP

(57) ABSTRACT

A fundus oculi observation device 1 can form a near-infrared motion image and a color image (still image) of a fundus oculi Ef. The device 1 specifies an image region within the near-infrared motion image corresponding to a region of interest within the color image while the near-infrared motion image is being formed. The device 1 scans with a signal light LS based on the specified image region, thereby forming a tomographic image along the scanning line. According to the device 1, it is possible to determine a region of interest within a still image having a comparatively high image quality, specify the image region within the motion image corresponding to this region of interest, set a measurement site for the tomographic image.

15 Claims, 18 Drawing Sheets

FUNDUS OCULI OBSERVATION DEVICE AND PROGRAM FOR CONTROLLING THE SAME

TECHNICAL FIELD

The present invention relates to a fundus oculi observation device for observing the fundus oculi of an eye, and to a program for controlling the fundus oculi observation device.

BACKGROUND ART

In recent years, the optical image measuring technology of forming an image showing the surface and internal morphology of a measurement object by using a light beam from a laser light source or the like has received attention. Since this optical image measuring technology does not have invasiveness against a human body unlike the X-ray CT, it is expected that application of this technique is developed especially in the medical field.

Patent Document 1 discloses an optical image measurement device having a configuration that: a measuring arm scans an object by a rotary conversion mirror (Galvano mirror); a reference arm is provided with a reference mirror; at the outlet, an interferometer in which the intensity of light appearing by interference of light fluxes from the measurement arm and the reference arm is analyzed by a spectrometer is used; and the reference arm is provided with a device that gradually changes the light flux phase of a reference light by discontinuous values.

The optical image measurement device disclosed in Patent Document 1 uses a method of so-called "Fourier Domain OCT (Optical Coherence Tomography)." In this method, by applying a low-coherence light beam to a measurement object, acquiring the spectrum intensity distribution of the reflected light, and executing Fourier transformation on the spectrum intensity distribution, the morphology in the depth direction (z-direction) of the measurement object is imaged.

Further, the optical image measurement device disclosed in Patent Document 1 is provided with a Galvano mirror for scanning with a light beam (signal light) and is thereby capable of forming an image of a desired measurement target region of a measurement object. Since this optical image measurement device scans with a light beam in only one direction (x-direction) orthogonal to the z-direction, a formed image is a two-dimensional tomographic image in the depth direction (z-direction) along a scanning direction (x-direction) of the light beam.

Patent Document 2 discloses a technology of forming a plurality of two-dimensional tomographic images in the horizontal direction by scanning with a signal light in the horizontal and vertical directions to acquire and image three-dimensional tomographic information of a measurement range based on the plurality of tomographic images. This three-dimensional imaging is executed by, for example, a method of arranging a plurality of tomographic images in the vertical direction and displaying the tomographic images (referred to as "stack data" or the like), or a method of executing a rendering process on a plurality of tomographic images and forming a three-dimensional image.

Patent Document 3 discloses a configuration in which the optical image measurement device as described above is applied in the ophthalmic field.

[Patent Document 1] Japanese Unexamined Patent Application Publication No. 11-325849

[Patent Document 2] Japanese Unexamined Patent Application Publication No. 2002-139421

[Patent Document 3] Japanese Unexamined Patent Application Publication No. 2003-543

DISCLOSURE OF THE INVENTION

Problem that the Invention is to Solve

In a case that a conventional optical image measurement device is applied to a fundus oculi observation, the following problem may occur. In a fundus oculi observation, there is an attention site to become an observation target, and it is necessary to certainly acquire an image of the attention site. For this purpose, a conventional device specifies an attention site while observing a motion image of the fundus oculi in real time and acquires a tomographic image of the attention site. The attention site is, for example, tissues of the fundus oculi such as the optic papilla, the macula and blood vessels, and also lesion sites such as retinal detachment, tumors, neovascularization and bleeding sites.

However, since a motion image for specifying an attention site is generally captured by using an illumination light of near-infrared region, the quality of the motion image is comparatively low, and therefore, it is difficult to accurately specify the attention site. Although capture of a motion image using an illumination light of visible region is possible, it is not preferable because there is a problem that it considerably burdens a subject due to glare and causes miosis of an eye.

Moreover, although alignment of the optical system of the device with respect to an eye is required for certain acquisition of an image of an attention site, this alignment operation is not easy because of the low quality of a motion image as described above and eye movement of the eye (including involuntary eye movement or the like).

The present invention was made for solving these problems. An object of the present invention is to provide a fundus oculi observation device that is capable of certainly acquiring an image of an attention site of the fundus oculi as compared with a conventional one, and also provide a program for controlling the fundus oculi observation device.

Means for Solving the Problem

In order to achieve the above object, in a first aspect of the present invention, a fundus oculi observation device has a forming part configured to form a motion image of a fundus oculi, an interference-light generator configured to split a low-coherence light into a signal light and a reference light and superimpose the signal light propagated through the fundus oculi and the reference light propagated through a reference object to generate an interference light, and a detector configured to detect the interference light, and forms a tomographic image of the fundus oculi based on a result of detection of the interference light, and the fundus oculi observation device comprises: a scanner configured to scan the fundus oculi with the signal light; a storage configured to store a still image of the fundus oculi; a specifying part configured to, when a motion image is being formed by the forming part, specify an image region in the motion image corresponding to a region of interest in the still image; and a controller configured to control the scanner to scan with the signal light based on the image region, and the fundus oculi observation device forming a tomographic image based on a result of detection of an interference light based on the scan signal light.

Further, in a second aspect of the present invention, the fundus oculi observation device according to the first aspect is characterized in that: the forming part is configured to form the motion image by successively forming frame images of the fundus oculi at a predetermined time interval; the specifying part is configured to specify an image region in one frame image corresponding to the region of interest in the still image and specify an image region in another frame image corresponding to the image region in the one frame image; and the controller is configured to scan with the signal light based on the image region in the other frame image.

Further, in a third aspect of the present invention, the fundus oculi observation device according to the first aspect is characterized in that the specifying part is configured to, for one frame image of a motion image formed by the forming part, specify an image region corresponding to the region of interest in the still image and, for each frame image formed later than the one frame image, specify an image region corresponding to the image region in the one frame image.

Further, in a fourth aspect of the present invention, the fundus oculi observation device according to the first aspect is characterized in that the specifying part includes an image display configured to display the still image and the motion image and a designating part for designating a region of interest in the displayed still image, and is configured to specify an image region in the motion image corresponding to the designated region of interest.

Further, in a fifth aspect of the present invention, the fundus oculi observation device according to the fourth aspect is characterized in that: the region of interest has a predetermined shape; the specifying part is configured to obtain a characteristic position in the region of interest according to the predetermined shape and obtain a position in the motion image corresponding to the characteristic position; and the controller is configured to control to scan with the signal light so as to pass through a position in the fundus oculi corresponding to the obtained position.

Further, in a sixth aspect of the present invention, the fundus oculi observation device according to the fifth aspect is characterized in that the predetermined shape is a substantially circular shape; the specifying part is configured to obtain a central position in the designated region of interest as the characteristic position and obtain a position in the motion image corresponding to the central position; and the controller is configured to control to scan with the signal light along a plurality of scanning lines arranged radially around a position in the fundus oculi corresponding to the position in the motion image.

Further, in a seventh aspect of the present invention, the fundus oculi observation device according to the fifth aspect is characterized in that the predetermined shape is a substantially circular shape; the specifying part is configured to obtain a central position in the designated region of interest as the characteristic position and obtain a position in the motion image corresponding to the central position; and the controller is configured to control to scan with the signal light along one or more circular scanning lines arranged around a position in the fundus oculi corresponding to the position in the motion image.

Further, in an eighth aspect of the present invention, the fundus oculi observation device according to the sixth aspect is characterized in that: the specifying part includes an extracting part configured to analyze the still image based on preset pixel value information and extract a region of interest and is configured to specify an image region in the motion image corresponding to the extracted region of interest.

Further, in a ninth aspect of the present invention, the fundus oculi observation device according to the first aspect further comprises: a fixation target projecting part configured to project a fixation target to the fundus oculi; a display configured to display the motion image; and an manipulation part, and is characterized in that: the controller is configured to control to display a preset size of frame-shaped image on the motion image and change a projection position of the fixation target to the fundus oculi in response to an operation from the manipulation part; and the projection position of the fixation target can be changed so that a region of interest in the motion image is placed in the frame-shaped image.

Further, in a tenth aspect of the present invention, the fundus oculi observation device according to the first aspect further comprises an alignment target projecting part configured to project, to the fundus oculi, an alignment target for adjusting a position of a device optical system with respect to an eye.

Further, in an eleventh aspect of the present invention, the fundus oculi observation device according to the first aspect is characterized in that the controller is configured to calculate a magnification of an ocular optical system of an eye and control to scan with the signal light based on the image region and the magnification.

Further, in a twelfth aspect of the present invention, the fundus oculi observation device according to the first aspect is characterized in that: the forming part is configured to capture a motion image of a surface of the fundus oculi by using an illumination light of near-infrared region; and the still image is a color image of the surface of the fundus oculi captured by using an illumination light of visible region, or a fluorescent image of the surface of the fundus oculi captured by administering a fluorescent agent to a subject.

Further, in a thirteenth aspect of the present invention, the fundus oculi observation device according to the first aspect is characterized in that: the forming part is configured to form a tomographic motion image of the fundus oculi; and the still image is a tomographic still image of the fundus oculi.

Further, in a fourteenth aspect of the present invention, the fundus oculi observation device according to the first aspect is characterized in that: the forming part is configured to form a still image of the fundus oculi while forming a motion image of the fundus oculi; and the specifying part is configured to specify an image region in the motion image corresponding to a region of interest in the still image.

Further, in a fifteenth aspect of the present invention, a program is configured to control a fundus oculi observation device that has: a forming part configured to form a motion image of a fundus oculi; an interference-light generator configured to superimpose the signal light propagated through the fundus oculi and the reference light propagated through a reference object to generate an interference light; a detector configured to detect the interference light; a scanner configured to scan the fundus oculi with the signal light; and a computer provided with a storage configured to store a still image of the fundus oculi, and the program makes the computer: function as a specifying part configured to, when a motion image is being formed by the forming part, specify an image region in the motion image corresponding to a region of interest in the still image; function as a controller configured to control to the scanner to scan with the signal light based on the image region; and function as an image forming part configured to form a tomographic image of the fundus oculi based on a result of detection of an interference light based on the scan signal light.

EFFECT OF THE INVENTION

According to the present invention, it is possible to, when a motion image is being formed, specify an image region in the motion image corresponding to a region of interest in a still image, control a scanner to scan with a signal light based on the image region, and form a tomographic image of the fundus oculi based on the result of detection of an interference light based on the signal light. A "region of interest" is an image region corresponding to an attention site of the fundus oculi.

According to the present invention, it is possible to determine a region of interest in a still image having a comparatively high image quality, specify an image region in a motion image corresponding to the region of interest, and set a measurement site of a tomographic image. Therefore, as compared with a conventional technique in which a measurement site is set with reference to only a motion image having a comparatively low image quality, it is possible to certainly acquire an image of an attention site of the fundus oculi.

BEST MODE FOR CARRYING OUT THE INVENTION

An example of an embodiment of a fundus oculi observation device and a program for controlling the fundus oculi observation device according to the present invention will be described in detail with reference to the drawings.

The fundus oculi observation device according to the present invention is configured so as to be capable of acquiring an image of an attention site of the fundus oculi by specifying an image region in a motion image of the fundus oculi corresponding to a region of interest in a still image of the fundus oculi and by scanning with a signal light based on the image region to form a tomographic image of the fundus oculi. Moreover, the fundus oculi observation device according to the present invention is for facilitating an alignment operation for acquiring an image of an attention site of the fundus oculi.

Attention sites of the fundus oculi are tissues of the fundus oculi such as the optic papilla, the macula and blood vessels, lesion sites such as retinal detachment, tumors, neovascularization and bleeding sites, and the like. A region of interest in a still image is an image region corresponding to an attention site in a still image of the fundus oculi. An image region is part of a certain image (still image, motion image) or the whole image.

[Device Configuration]

The configuration of an embodiment of the fundus oculi observation device according to the present invention will be described with reference to FIGS. 1~8. FIG. 1 shows an example of the entire configuration of a fundus oculi observation device 1 according to this embodiment. FIG. 2 shows an example of the configuration of an alignment optical system 190A in a retinal camera unit 1A. FIG. 3 shows an example of an alignment operation using the alignment optical system. FIG. 4 shows an example of the configuration of a scan unit 141 in the retinal camera unit 1A. FIG. 5 shows an example of the configuration of an OCT unit 150. FIG. 6 shows an example of the hardware configuration of an arithmetic and control unit 200. FIGS. 7 and 8 show an example of the configuration of a control system of the fundus oculi observation device 1.

[Entire Configuration]

As shown in FIG. 1, the fundus oculi observation device 1 includes the retinal camera unit 1A, the OCT unit 150, and the arithmetic and control unit 200. The retinal camera unit 1A has an optical system that is mostly similar to that of a conventional retinal camera that captures a two-dimensional image of the fundus oculi surface. The OCT unit 150 houses an optical system that functions as an optical image measurement device. The arithmetic and control unit 200 is provided with a computer that executes various arithmetic processes, control processes, and so on.

One end of a connection line 152 is attached to the OCT unit 150. A connector 151 that connects the connection line 152 to the retinal camera unit 1A is attached to the other end of the connection line 152. An optical fiber is conductively passed through the inside of the connection line 152. Thus, the OCT unit 150 and the retinal camera unit 1A are optically connected via the connection line 152.

[Configuration of Retinal Camera Unit]

The retinal camera unit 1A is used to form a two-dimensional image of the surface of the fundus oculi of an eye, based on optically acquired data (data detected by imaging devices 10 and 12). A two-dimensional image of the surface of the fundus oculi is, for example, a color or monochrome image obtained by capturing the surface of the fundus oculi, and a fluorescent image (a fluorescein angiography image, an indocyanine green fluorescent image and the like). Like a conventional retinal camera, the retinal camera unit 1A is provided with an illumination optical system 100 that applies an illuminate light to a fundus oculi Ef, and an imaging optical system 120 that guides the fundus oculi reflected light of the illumination light to the imaging device 10.

Although the details will be described later, the imaging device 10 in the imaging optical system 120 detects an illumination light having a wavelength of near-infrared region. The imaging optical system 120 is also provided with the imaging device 12 that detects an illumination light having a wavelength of visible region. The imaging optical system 120 acts to guide a signal light coming from the OCT unit 150 to the fundus oculi Ef and also guide the signal light propagated through the fundus oculi Ef to the OCT unit 150.

The illumination optical system 100 includes an observation light source 101, a condenser lens 102, an imaging light source 103, a condenser lens 104, exciter filters 105 and 106, a ring transparent plate 107, a mirror 108, an LCD (Liquid Crystal Display) 109, an illumination diaphragm 110, a relay lens 111, an aperture mirror 112, and an objective lens 113.

The observation light source 101 emits an illumination light having a wavelength of visible region included in a range of, for example, about 400~700 nm. The imaging light source 103 emits an illumination light having a wavelength of near-infrared region included in a range of, for example, about 700~800 nm. The near-infrared light emitted from the imaging light source 103 is set so as to have a shorter wavelength than a light used by the OCT unit 150 (described later).

The imaging optical system 120 includes an objective lens 113, the (aperture 112a of) aperture mirror 112, an imaging diaphragm 121, barrier filters 122 and 123, a variable magnifying lens 124, a relay lens 125, an imaging lens 126, a dichroic mirror 134, a field lens 128, a half mirror 135, a relay lens 131, a dichroic mirror 136, an imaging lens 133, the imaging device 10 (an image pick-up element 10a), a reflection mirror 137, an imaging lens 138, the imaging device 12 (an image pick-up element 12a), a lens 139, and an LCD 140.

Further, the imaging optical system 120 is provided with the dichroic mirror 134, the half mirror 135, the dichroic mirror 136, the reflection mirror 137, the imaging lens 138, the lens 139, and the LCD 140.

The dichroic mirror 134 is configured to reflect the fundus oculi reflected light (having a wavelength included in a range of about 400~800 nm) of the illumination light coming from the illumination optical system 100 and to transmit a signal light LS (having a wavelength included in a range of, for example, about 800~900 nm; described later) coming from the OCT unit 150.

Further, the dichroic mirror 136 is configured to transmit the illumination light having a wavelength of visible region coming from the illumination optical system 100 (a visible light having a wavelength of about 400~700 nm emitted from the observation light source 101) and to reflect the illumination light having a wavelength of near-infrared region (a near-infrared light having a wavelength of about 700~800 nm emitted from the imaging light source 103).

The LCD 140 displays a fixation target (internal fixation target) or the like for fixing an eye E. The light from the LCD 140 is reflected by the half mirror 135 after being converged by the lens 139, and is reflected by the dichroic mirror 136 through the field lens 128. This light is propagated through the imaging lens 126, the relay lens 125, the variable magnifying lens 124, the (aperture 112a of the) aperture mirror 112, the objective lens 113 and so on, and enters the eye E. Consequently, an internal fixation target is projected on the fundus oculi Ef of the eye E. The LCD 140 and these optical elements configure an example of the "fixation target projecting part" of the present invention.

The image pick-up element 10a is an image pick-up element such as a CCD and a CMOS installed in the imaging device 10 such as a TV camera, and particularly detects a light having a wavelength of near-infrared region. That is, the imaging device 10 is an infrared TV camera that detects a near-infrared light. The imaging device 10 outputs video signals as the result of detection of the near-infrared light.

A touch panel monitor 11 displays a two-dimensional image (a fundus oculi image Ef) of the surface of the fundus oculi Ef, based on the video signals. The video signals are also sent to the arithmetic and control unit 200, and a fundus oculi image is displayed on a display (described later).

For fundus oculi imaging by the imaging device 10, for example, an illumination light having a wavelength of near-infrared region emitted from the imaging light source 103 of the illumination optical system 100 is used.

On the other hand, the image pick-up element 12a is an image pick-up element such as a CCD and a CMOS installed in the imaging device 12 such as a TV camera, and particularly detects a light having a wavelength of visible region. That is to say, the imaging device 12 is a TV camera that detects a visible light. The imaging device 12 outputs video signals as the result of detection of the visible light.

The touch panel monitor 11 displays a two-dimensional image of the surface of the fundus oculi Ef (the fundus oculi image Ef'), based on the video signals. The video signals are also sent to the arithmetic and control unit 200, and a fundus oculi image is displayed on the display (described later).

For fundus oculi imaging by the imaging device 12, for example, an illumination light having a wavelength of visible region emitted from the observation light source 101 of the illumination optical system 100 is used.

The retinal camera unit 1A is provided with a scan unit 141 and a lens 142. The scan unit 141 includes a configuration for scanning an application position to the fundus oculi Ef of a light emitted from the OCT unit 150 (signal light LS; described later). The scan unit 141 is an example of the "scanner" of the present invention.

The lens 142 collimates the signal light LS guided through the connection line 152 from the OCT unit 150 and makes the light enter the scan unit 141. Moreover, the lens 142 focuses the fundus oculi reflected light of the signal light LS propagated through the scan unit 141.

FIG. 4 shows an example of the configuration of the scan unit 141. The scan unit 141 includes Galvano mirrors 141A and 141B, and reflection mirrors 141C and 141D.

The Galvano mirrors 141A and 141B are reflection mirrors disposed so as to be rotatable around rotary shafts 141a and 141b, respectively. The Galvano mirrors 141A and 141B are respectively rotated around the rotary shafts 141a and 141b by drive mechanisms, which will be described later (mirror drive mechanisms 241 and 242 shown in FIG. 7). Thus, a direction in which the reflected surface (a surface that reflects the signal light LS) of each of the Galvano mirrors 141A and 141B faces is changed.

The rotary shafts 141a and 141b are arranged orthogonally to each other. In FIG. 4, the rotary shaft 141a of the Galvano mirror 141A is arranged in the parallel direction to the paper face. On the other hand, the rotary shaft 141b of the Galvano mirror 141B is arranged in the orthogonal direction to the paper face.

That is to say, the Galvano mirror 141B is configured so as to be rotatable in the directions indicated by an arrow pointing in both directions in FIG. 4, whereas the Galvano mirror 141A is configured so as to be rotatable in the directions orthogonal to the arrow pointing in both the directions. Consequently, the Galvano mirrors 141A and 141B respectively act so as to change directions of reflection of the signal light LS into directions orthogonal to each other. As can be seen in FIGS. 1 and 4, a scan with the signal light LS is performed in the x-direction when the Galvano mirror 141A is rotated, whereas a scan with the signal light LS is performed in the y-direction when the Galvano mirror 141B is rotated.

The signal light LS reflected by the Galvano mirrors 141A and 141B is reflected by the reflection mirrors 141C and 141D, thereby traveling in the same direction as having entered the Galvano mirror 141A.

An end face 152b of the optical fiber 152a inside the connection line 152 is arranged facing the lens 142. The signal light LS emitted from the end face 152b travels expanding its beam diameter toward the lens 142, and is collimated by the lens 142. On the contrary, the signal light LS propagated through the fundus oculi Ef is focused to the end face 152b by the lens 142, and enters the optical fiber 152a.

A half mirror 190 is disposed in the slanted state on an optical path between the variable magnifying lens 124 and the relay lens 125. The half mirror 190 acts to synthesize the optical path of the alignment optical system 190A shown in FIG. 2A and the optical path of the imaging optical system 120 (imaging optical path). The alignment optical system 190A is an optical system for projecting, onto the eye E, an alignment bright point used in alignment of the optical system with the eye E.

This alignment bright point is used for both alignment of matching the top of the cornea of the eye E with the optical axes of the optical systems 100 and 120 (alignment in the xy-directions shown in FIG. 1) and alignment of a distance between the eye E and the optical systems 100 and 120 (the z direction in FIG. 1; working distance; a distance between the (top of the) cornea of the eye E and the objective lens 113) (refer to Japanese Unexamined Patent Application Publication No. 11-4808, for example). This alignment bright point is an example of the "alignment target" of the present invention.

The alignment optical system 190A includes an alignment light source 190a, a light guide 190b, a reflection mirror 190c, a two-hole aperture 190d, and a relay lens 190e, as well as the half mirror 190, as shown in FIG. 2A. The alignment light source 190a is configured by, for example, a light source such as an LCD that emits a light of near-infrared region (alignment light).

The two-hole aperture 190d has two holes 190d1 and 190d2 as shown in FIG. 2B. The holes 190d1 and 190d2 are formed at symmetric positions with respect to a center position 190*d*3 of the circular two-hole aperture 190*d*, for example. The two-hole aperture 190*d* is arranged so that the center position 190*d*3 is located on the optical axis of the alignment optical system 190A.

The alignment light ejected from an ejection end 190β of the light guide 190*b* is reflected by the reflection mirror 190*c* and guided to the two-hole aperture 190*d*. (Part of) the alignment light passed through the holes 190*d*1 and 190*d*2 of the two-hole aperture 190*d* is, propagated through the relay lens 190*e*, reflected by the half mirror 190, and guided to the aperture mirror 112. During this time, the relay lens 190*e* makes an image of the ejection end 190β of the light guide 190*b* intermediately focus on the center position of the aperture 112*a* of the aperture mirror 112 (a position on the optical axis of the imaging optical system 120). The alignment light passed through the aperture 112*a* of the aperture mirror 112 is projected to the cornea of the eye E via the objective lens 113.

When the positional relation between the eye E and the retinal camera unit 1A (the objective lens 113) is proper, namely, when the distance between the eye E and the retinal camera unit 1A (the working distance) is proper and the optical axis of the optical system of the retinal camera unit 1A and the eye axis of the eye E (top position of the cornea) are (substantially) coincident with each other, two light fluxes formed by the two-hole aperture 190*d* (alignment light fluxes) are projected to the eye E so as to be focused at the intermediate position between the top of the cornea and the center of corneal curvature.

The corneal reflected lights of the two alignment light fluxes (alignment lights) are received by the imaging devices 10*a* via the imaging optical system 120. An image captured by the imaging device 10*a* is displayed on a display device such as the touch panel monitor 11 or the display of the arithmetic and control unit 200 (described later). A display pattern of the alignment light at this time is shown in FIGS. 3A and 3B.

A symbol S in FIGS. 3A and 3B denotes a scale having a bracket shape, and symbols P1 and P2 denote the light-receiving image of the two alignment light fluxes (alignment bright points). The scale S is displayed on the display or the like so that its center position coincides with the optical axis of the imaging optical system 120.

When the position of the eye E and the position of the retinal camera unit 1A are misaligned in the up-and-down direction (y-direction) or the right-and-left direction (x-direction), the alignment bright points P1 and P2 are displayed in positions misaligned in the up-and-down direction or the right-and-left direction with respect to the scale S as shown in FIG. 3A. When the working distance is not proper, the alignment bright points P1 and P2 are displayed at separate positions, respectively.

On the other hand, when the positions in the xy directions of the eye E and the retinal camera unit 1A coincide with each other and the working distance is proper, the alignment bright points P1 and P2 are displayed within the scale S in the mutually overlapping state as shown in FIG. 3B. An examiner executes the alignment by regulating the positional relation between the eye E and the retinal camera unit 1A so that the alignment bright points P1 and P2 overlap each other and are displayed within the scale S.

The optical elements of the alignment optical system 190A and the imaging optical system 120 for guiding the alignment light to the fundus oculi Ef configure an example of the "alignment target projecting part" of the present invention.

[Configuration of OCT Unit]

Next, the configuration of the OCT unit 150 will be described with reference to FIG. 5. The OCT unit 150 is a device for forming a tomographic image of the fundus oculi based on optically acquired data (data detected by a CCD 184 described later).

The OCT unit 150 has almost the same optical system as a conventional optical image measurement device. That is to say, the OCT unit 150 splits a low-coherence light into a reference light and a signal light and superimposes the signal light propagated through an eye with the reference light propagated through a reference object, thereby generating and detecting an interference light. The detection result (a detection signal) is inputted to the arithmetic and control unit 200. The arithmetic and control unit 200 analyzes the detection signal and form a tomographic image of the eye.

A low-coherence light source 160 is configured by a broadband light source such as a super luminescent diode (SLD) or a light emitting diode (LED), which outputs a low-coherence light L0. The low-coherence light L0 is, for example, a light including a light having a wavelength of near-infrared region and having a temporal coherence length of approximately several tens of micrometers.

The low-coherence light L0 has a longer wavelength than the illumination light of the retinal camera unit 1A (a wavelength of about 400~800 nm), for example, a wavelength included in a range of about 800~900 nm.

The low-coherence light L0 outputted from the low-coherence light source 160 is guided to an optical coupler 162 through an optical fiber 161. The optical fiber 161 is configured by, for example, a single mode fiber or a PM (Polarization maintaining) fiber. The optical coupler 162 splits the low-coherence light L0 into a reference light LR and the signal light LS.

Although the optical coupler 162 acts as both a part that splits a light (a splitter) and a part that superimposes lights (a coupler), it will be hereinafter referred to as an "optical coupler" idiomatically.

The reference light LR generated by the optical coupler 162 is guided by an optical fiber 163 configured by a single mode fiber or the like, and emitted from the end face of the fiber. Furthermore, the reference light LR is collimated by a collimator lens 171, propagated through a glass block 172 and a density filter 173, and reflected by a reference mirror 174. The reference mirror 174 is an example of the "reference object" of the present invention.

The reference light LR reflected by the reference mirror 174 is again propagated through the density filter 173 and the glass block 172, focused to the fiber end face of the optical fiber 163 by the collimator lens 171, and guided to the optical coupler 162 through the optical fiber 163.

The glass block 172 and the density filter 173 act as a delaying part for matching the optical path lengths (optical distances) of the reference light LR and the signal light LS, and also as a dispersion compensation part for matching the dispersion characteristics of the reference light LR and the signal light LS.

The density filter 173 also acts as a neutral density filter that reduces the light amount of a reference light, and is configured by, for example, a rotatable ND (Neutral Density) filter. The density filter 173 is driven to rotate by a drive mechanism (a density filter drive mechanism 244 described later; refer to FIG. 7) that includes a driver such as a motor, thereby acting to change the reduction amount of the light amount of the reference light LR. Consequently, it is possible to change the light amount of the reference light LR that contributes to generation of the interference light LC.

The reference mirror 174 is configured to move in the traveling direction of the reference light LR (the direction of the arrow pointing both sides shown in FIG. 5). Thus, it is possible to ensure the optical path length of the reference light LR corresponding to the eye axial length of the eye E, the working distance (the distance between the objective lens 113 and the eye E), and so on. Moreover, by moving the reference mirror 174, it is possible to acquire an image of the fundus oculi Ef at an arbitrary depth position. The reference mirror 174 is moved by a drive mechanism (a reference-mirror drive mechanism 243 described later; refer to FIG. 7) that includes a driver such as a motor.

On the other hand, the signal light LS generated by the optical coupler 162 is guided to the end of the connection line 152 through an optical fiber 164 configured by a single mode fiber or the like. The conductive optical fiber 152a runs inside the connection line 152. The optical fiber 164 and the optical fiber 152a may be composed of a single optical fiber, or may be integrally formed by connecting the end faces of the respective fibers. In either case, it is sufficient as far as the optical fiber 164 and 152a are configured to be capable of transferring the signal light LS between the retinal camera unit 1A and the OCT unit 150.

The signal light LS is led through the inside of the connection line 152 and guided to the retinal camera unit 1A. Furthermore, the signal light LS is propagated through the lens 142, the scan unit 141, the dichroic mirror 134, the imaging lens 126, the relay lens 125, the variable magnifying lens 124, the imaging diaphragm 121, the aperture 112a of the aperture mirror 112 and the objective lens 113, and applied to the eye E. When the signal light LS is applied to the eye E, the barrier filter 122 and 123 are retracted from the optical paths in advance, respectively.

The signal light LS having entered the eye E forms an image on the fundus oculi Ef and is then reflected. In this case, the signal light LS is not only reflected on the surface of the fundus oculi Ef, but also scattered at the refractive index boundary after reaching the deep area of the fundus oculi Ef. Therefore, the signal light LS propagated through the fundus oculi Ef contains information reflecting the morphology of the surface of the fundus oculi Ef and information reflecting the state of backscatter at the refractive index boundary of the deep area tissue of the fundus oculi Ef. This light may be simply referred to as the "fundus oculi reflected light of the signal light LS."

The fundus oculi reflected light of the signal light LS reversely travels along the abovementioned path within the retinal camera unit 1A, and is focused to the end face 152b of the optical fiber 152a. Then, the signal light LS enters the OCT unit 150 through the optical fiber 152a, and returns to the optical coupler 162 through the optical fiber 164.

The optical coupler 162 superimposes the signal light LS returned through the eye E and the reference light LR reflected by the reference mirror 174, thereby generating the interference light LC. The generated interference light LC is guided to a spectrometer 180 through an optical fiber 165 configured by a single mode fiber or the like.

Although a Michelson type interferometer is adopted in the present embodiment, it is possible to adopt any type of interferometer such as a Mach Zender type as necessary.

The "interference-light generator" in the present invention includes, for example, the optical coupler 162, an optical member on the optical path of the signal light LS (namely, an optical member disposed between the optical coupler 162 and the eye E), and an optical member on the optical path of the reference light LR (namely, an optical member disposed between the optical coupler 162 and the reference mirror 174). To be specific, the interference-light generator includes an interferometer provided with the optical coupler 162, the optical fibers 163 and 164 and the reference mirror 174.

The spectrometer 180 includes a collimator lens 181, a diffraction grating 182, an image forming lens 183, and a CCD 184. The diffraction grating 182 may be a transmission-type diffraction grating that transmits light, or may be a reflection-type diffraction grating that reflects light. Besides, it is possible to use, instead of the CCD 184, another photo-detecting element such as a CMOS.

The interference light LC entered the spectrometer 180 is collimated by the collimator lens 181 and split (subjected to spectral resolution) by the diffraction grating 182. The split interference light LC is formed into an image on the image pick-up face of the CCD 184 by the image forming lens 183. The CCD 184 detects the respective spectra of the split interference light LC and converts them into electrical signals, and outputs the detection signals to the arithmetic and control unit 200. The CCD 184 is an example of the "detector" of the present invention.

[Configuration of Arithmetic and Control Unit]

Next, the configuration of the arithmetic and control unit 200 will be described. The arithmetic and control unit 200 analyzes detection signals inputted from the CCD 184 of the OCT unit 150, and forms a tomographic image of the fundus oculi Ef. The analysis method in this case is the same as in the conventional Fourier Domain OCT method.

Further, the arithmetic and control unit 200 forms a two-dimensional image showing the morphology of the surface of the fundus oculi Ef, based on the video signals outputted from the imaging devices 10 and 12 of the retinal camera unit 1A. The two-dimensional image may be a still image or a motion image. Control of the light sources 101 and 103 and the imaging devices 10 and 12 for acquiring the image is executed by a microprocessor 201 (a controller 210), which will be described later.

The arithmetic and control unit 200 controls each part of the retinal camera unit 1A and the OCT unit 150.

As the control of the retinal camera unit 1A, the arithmetic and control unit 200 executes, for example: control of emission of the illumination light by the observation light source 101 or the imaging light source 103; control of the insertion/retraction operations of the exciter filters 105 and 106 or the barrier filters 122 and 123 to/from the optical path; control of the operation of a display device such as the LCD 140; control of movement of the illumination diaphragm 110 (control of the diaphragm value); control of the diaphragm value of the imaging diaphragm 121; and control of movement of the variable magnifying lens 124. Furthermore, the arithmetic and control unit 200 executes control of the operation of the Galvano mirrors 141A and 141B.

On the other hand, as the control of the OCT unit 150, the arithmetic and control unit 200 executes, for example: control of emission of the low-coherence light L0 by the low-coherence light source 160; control of movement of the reference mirror 174; control of the rotation operation of the density filter 173 (the operation of changing the reduction amount of the light amount of the reference light LR); and control of the accumulated time of the CCD 184.

The hardware configuration of the arithmetic and control unit 200 as described above will be described referring to FIG. 6.

The arithmetic and control unit 200 has the same hardware configuration as that of a conventional computer. To be specific, the arithmetic and control unit 200 includes a microprocessor 201, a RAM 202, a ROM 203, a hard disk drive (HDD)

204, a keyboard 205, a mouse 206, a display 207, an image forming board 208, and a communication interface (I/F) 209. The respective parts are connected via a bus 200a.

The microprocessor 201 includes a CPU (central processing unit), an MPU (micro processing unit) or the like. The microprocessor 201 executes operations characteristic to the present embodiment, by loading a control program 204a stored in the hard disk drive 204, onto the RAM 202.

Further, the microprocessor 201 executes control of each part of the device described above, various arithmetic processes, and so on. Moreover, the microprocessor 201 controls each part of the device in accordance with an operation content in response to an operation signal from the keyboard 205 or the mouse 206. Besides, the microprocessor 201 executes control of a display process by the display 207, control of a transmission/reception process of data and signals by the communication interface 209, and so on.

The keyboard 205, the mouse 206, and the display 207 are used as user interfaces in the fundus oculi observation device 1. The keyboard 205 is used as, for example, a device for typing letters, figures, or the like. The mouse 206 is used as a device for performing various input operations to the display screen of the display 207.

Further, the display 207 is a display device such as an LCD or a CRT (Cathode Ray Tube) display. The display 207 displays various images such as an image of the fundus oculi Ef formed by the fundus oculi observation device 1, and displays various screens such as an operation screen and a set-up screen.

The user interface of the fundus oculi observation device 1 is not limited to the above configuration, and may be configured to include a track ball, a control lever, a touch panel type of LCD, and a control panel for ophthalmic examination. As the user interface, it is possible to adopt any configuration provided with a function of displaying and outputting information and a function of inputting information or operating the device.

The image forming board 208 is a dedicated electronic circuit for a process of forming (image data of) an image of the fundus oculi Ef. The image forming board 208 is provided with a fundus oculi image forming board 208a and an OCT image forming board 208b.

The fundus oculi image forming board 208a is a dedicated electronic circuit for forming image data of a fundus oculi image based on video signals from the imaging device 10 and the imaging device 12.

On the other hand, the OCT image forming board 208b is a dedicated electronic circuit for forming image data of a tomographic image of the fundus oculi Ef, based on the detection signals from the CCD 184 of the OCT unit 150.

By disposing the image forming board 208, it is possible to increase the processing speed for forming a fundus oculi image and a tomographic image.

The communication interface 209 transmits control signals from the microprocessor 201, to the retinal camera unit 1A and the OCT unit 150. Moreover, the communication interface 209 receives video signals from the imaging devices 10 and 12 and detection signals from the CCD 184 of the OCT unit 150, and inputs the signals to the image forming board 208. In this case, the communication interface 209 inputs the video signals from the imaging devices 10 and 12, to the fundus oculi image forming board 208a, and inputs the detection signal from the CCD 184, to the OCT image forming board 208b.

Further, in a case that the arithmetic and control unit 200 is connected to a communication line such as a LAN (Local Area Network) and the Internet, it is possible to configure so as to be capable of data communication via the communication line by providing the communication interface 209 with a network adapter like a LAN card or communication equipment like a modem. In this case, by mounting a server accommodating the control program 204a on the communication line and configuring the arithmetic and control unit 200 as a client terminal of the server, it is possible to make the fundus oculi observation device 1 operate.

[Configuration of Control System]

Next, the configuration of the control system of the fundus oculi observation device 1 will be described referring to FIGS. 7 and 8.

(Controller)

The control system of the fundus oculi observation device 1 is configured mainly having the controller 210 of the arithmetic and control unit 200. The controller 210 includes the microprocessor 201, the RAM 202, the ROM 203, the hard disk drive 204 (the control program 204a), and the communication interface 209.

The controller 210 executes the aforementioned controls through the microprocessor 201 that operates based on the control program 204a. The controller 210 is provided with a main controller 211, a storage 212, a scan setting part 213, and a magnification calculator 214.

The main controller 211 controls the mirror drive mechanisms 241 and 242 to control the positions of the Galvano mirrors 141A and 141B, thereby scanning the fundus oculi Ef with the signal light LS.

Moreover, the main controller 211 controls the LCD 140 to display an internal fixation target for fixing the eye E at various fixation positions. An example of the fixation position is, for example, a fixation position for acquiring an image of the optic papilla of the fundus oculi Ef, a fixation position for acquiring an image of the macula, and so on. It is also possible to fix the eye E at an arbitrary fixation position. For this purpose, it is possible to configure so that a projection position of an internal fixation target on the fundus oculi Ef can be changed, by operating the manipulation part 240B, for example. Moreover, it is possible to configure so that a projection position of an internal fixation target can be changed based on previous fixation position information or the like stored in the storage 212.

Further, the main controller 211 executes control of each part of the device, such as control of turning on/off the low-coherence light source 160, control of the CCD 184, control of the density filter drive mechanism 244 for rotating the density filter 173, control of the reference-mirror drive mechanism 243 for moving the reference mirror 174 in the travelling direction of the reference light LR, control of turning on/off the observation light source 101 and the imaging light source 103, and control of the turning on/off the alignment light source 190a.

Further, the main controller 211 controls the display 240A of the user interface (UI) 240 to display two kinds of images captured by the fundus oculi observation device 1, namely, the fundus oculi image Ef' and a tomographic image. These images may be displayed separately, or may be displayed side by side. The fundus oculi image Ef' and the tomographic image may be a still image or a motion image.

The main controller 211 includes the microprocessor 201. The main controller 211 is an example of the "controller" of the present invention.

The storage 212 stores images (still images, motion images) formed by the image forming part 220 and the image processor 230. Furthermore, the storage 212 stores various types of data, such as information set by the scan setting part 213 and information calculated by the magnification calculator 214. A process of writing data into the storage 212 and a process of reading out data from the storage 212 are executed by the main controller 211.

The storage 212 includes storage devices such as the RAM 202, the ROM 203 and the hard disk drive 204 (in particular, the hard disk drive 204). The storage 212 is an example of the "storage" of the present invention.

The scan setting part 213 sets information regarding a scan with the signal light LS. For example, the scan setting part 213 sets scanning points, scanning lines and scanning regions of the signal light LS. These processes will be described in detail later. The scan setting part 213 configures an example of the "controller" of the present invention, together with the main controller 211.

The magnification calculator 214 calculates the magnification by the eye optical system of the eye. The magnification calculator 214 calculates the magnification based on predetermined optical information. The optical information is, for example, acquired by measurements in advance and stored into the storage 212. In the optical information, information such as measured values of the cornea curvature, refractive power and axial length of the eye E, existence of an intraocular lens, and the diopter power of the intraocular lens are recorded. Hereinafter, an example of a process executed by the magnification calculator 214 will be described. In the present embodiment, both the magnification by the eye E and the magnification by the imaging optical system 120 are considered in obtaining the imaging magnification.

First, in a case that the refractive power is a measured value at the corneal apex (corneal refractive power), the magnification calculator 214 converts it to the refractive power at the pupil (pupil refractive power) as needed. This calculation can be executed based on, for example, a spectacle wearing distance and a distance from the corneal apex to the entrance pupil as conventional.

Next, the magnification calculator 214 calculates the imaging position of a fundus oculi image by the objective lens 113. This calculation can be executed by the Newton equation based on, for example, the pupil refractive power, the focal length of the objective lens 113, and a distance from the entrance pupil to the anterior focus of the objective lens 113.

Next, the magnification calculator 214 calculates the photographing magnification of the variable magnification lens 124. This calculation can be executed by, for example, solving a quadratic equation representing a relation of the calculation result of the imaging position by the objective lens 113 and the focal distance, principal focal length and overall distance of the variable magnification lens 124, for the photographing magnification.

Next, the magnification calculator 214 calculates an exit angle from the objective lens 113. This calculation can be executed based on, for example, the result of calculation of the photographing magnification, a distance from the posterior principal point of the objective lens 113 to the imaging diaphragm 121, and the focal length of the objective lens 113. In this case, the exit angle is calculated so that the height of an image on the detection surface of the image becomes a predetermined value. This predetermined value is set to, for example, −0.1 mm (the minus sign indicates that the image is formed in the downward direction (−y-direction) from the optical axis).

Next, the magnification calculator 214 calculates an incident angle to the objective lens such that the height of an image on the diaphragm surface of the imaging diaphragm 121 becomes the abovementioned predetermined value. This calculation can be executed based on, for example, the result of calculation of the exit angle from the objective lens 113 and the angular magnification of the entrance pupil and the imaging diaphragm 121.

Next, the magnification calculator 214 calculates the radius of curvature of the rear surface of the cornea of the eye E. This calculation can be executed based on, for example, the measured value of the cornea curvature (curvature of the front surface of the cornea) recorded in the optical information, and the ratio between the curvatures of the front surface and the rear surface of the cornea. As the ratio of the curvature, it is possible to use, for example, a standard value based on clinical data, an eye model, and so on. In the case of measuring the curvature (radius of curvature) of the rear surface of the cornea by using an OCT device for cornea, it is possible to use the measured value as the radius of curvature of the rear surface of the cornea.

Next, the magnification calculator 214 calculates the distance between a far point and an object (cornea apex). This calculation can be executed based on, for example, the refractive power at the cornea apex, and the spectacle wearing distance.

Next, the magnification calculator 214 calculates the distance from the rear surface of the lens of the eye E to the retinal surface (fundus oculi Ef). This calculation can be executed, for example, by paraxial ray tracing based on the measured value and calculated value of the curvature (radius of curvature) of the cornea. In this case, as an ocular optical constant, for example, a standard value based on clinical data, an eye model and so on can be used.

Next, the magnification calculator 214 calculates the axial length of the eye E. This calculation can be executed based on, for example, the result of calculation of the paraxial ray tracing, and the distance from the front surface of the cornea to the rear surface of the lens. As this distance, it is possible to use, for example, a standard value based on clinical data, an eye model and so on.

Next, the magnification calculator 214 calculates the discrepancy between the calculation result of the axial length and the measurement result of the axial length (optical information), and determines whether this discrepancy falls within a predetermined acceptable range. As this discrepancy, for example, the discrepancy of the calculation result against the measured value, namely, the absolute value of the result of dividing the difference between the measured value and the calculation result by the measured value, is obtained. Further, the acceptable range of the discrepancy is preset as a threshold value for determining a value to be used as an optical constant of the ocular optical system of the eye E.

In a case that the axial length discrepancy falls within the acceptable range, for example, the measured value and calculation result of the curvature (radius of curvature) of the cornea, the measured value of the refractive power, and the calculation result of the axial length are used as the optical constant of the eye E. Moreover, a half value of the calculation result of the axial length is used as the radius of curvature of the retinal surface (fundus oculi Ef). Further, as the distance from the rear surface of the lens to the retina (fundus oculi Ef), a value obtained by subtracting a standard value (clinical data and an eye model value) of the distance from the corneal front surface to the rear surface of the lens from the calculation result of the axial length is used.

On the other hand, in a case that the discrepancy of the axial length does not fall within the acceptable range, the refractive power of the lens of the eye E is calculated by paraxial reverse ray tracing using the measured values of the apex refractive power and the axial length. Then, as an optical constant of the eye E, for example, the measured value and calculation result of the curvature (radius of curvature) of the cornea, and the measured values of the refractive power and axial length are used. Further, as the radius of curvature of the retinal surface (fundus oculi Ef), a half value of the measured value of the axial length is used. Further, as the distance from the rear surface of the lens to the retina (fundus oculi Ef), a value obtained by subtracting a standard value (clinical data and an eye model value) of the distance from the corneal front surface to the rear surface of the lens from the measured value of the axial length is used.

When the optical constant of the eye E is determined, the magnification calculator 214 calculates the height of an image on the retinal surface (fundus oculi Ef). This calculation can be executed by, for example, ray tracing using the determined optical constant and the result of calculation of the incident angle to the objective lens 113.

Finally, the magnification calculator 214 calculates the target magnification based on the calculation result of the height of the image on the retinal surface, the calculation result of the height of the image on the detection surface, and the relay magnification of a relay lens 126 (the influence of the imaging optical system 120 and so on). This magnification is obtained considering the magnification of the ocular optical system of the eye E and the magnification of the imaging optical system 120.

Above, the process of calculating magnification in a case that an intraocular lens is not placed on the eye E has been described. In a case that an intraocular lens is placed on the eye E, the magnification calculator 214 obtains magnification by executing the calculation as described above using information such as the diopter power of the intraocular lens. The existence of an intraocular lens is determined based on intraocular lens information.

Further, in a case that a correction lens is used, the magnification calculator 214 calculates the magnification of the correction lens and, considering the result of this calculation, executes the calculation as described above, thereby obtaining the target magnification. The magnification of the correction lens can be calculated based on the focal length of the correction lens, the distance between the focus on the objective lens 113 side and the principal point on the object side of the correction lens, and so on.

The magnification calculator 214 includes a microprocessor 201, a RAM 202 and so on. The magnification calculator 214 configures an example of the "controller" of the present invention, together with the main controller 211.

(Image Forming Part)

The image forming part 220 forms image data of the fundus oculi image Ef' based on video signals from the imaging devices 10 and 12. In the case of imaging with the imaging device 10, an illumination light is emitted from the imaging light source 103. Thus, a motion image of the fundus oculi Ef using a near-infrared light is obtained. It is also possible to obtain a still image using a near-infrared light. On the other hand, in the case of imaging by the imaging device 12, an illumination light is emitted from the observation light source 101. Thus, a still image (color image) of the fundus oculi Ef using a visible light is obtained. It is also possible to obtain a motion image using a visible light.

In the case of fluorescent imaging, the imaging light source 103 and the imaging device 10 are used for infrared fluorescent imaging, whereas the observation light source 101 and the imaging device 12 are used for visible fluorescent imaging. An image obtained by fluorescent imaging may be a still image or a motion image.

Further, the image forming part 220 forms image data of a tomographic image of the fundus oculi Ef, based on a detection signal from the CCD 184 of OCT unit 150.

The image forming part 220 includes the image forming board 208, the communication interface 209 and so on. In this specification, "image" may be identified with "image data" corresponding thereto.

The image forming part 220, together with optical members (the imaging light source 103, the imaging device 10 and so on) in the retinal camera unit 1A for obtaining a motion image, configures an example of the "forming part" of the present invention.

(Image Processor)

The image processor 230 executes various kinds of image processing and analysis on the image data of images formed by the image forming part 220. For example, the image processor 230 executes various kinds of correction processes such as luminance correction of images and dispersion correction.

Further, the image processor 230 forms image data of three-dimensional images of the fundus oculi Ef by executing, for example, an interpolation process of interpolating pixels between tomographic images on the tomographic images formed by the image forming part 220.

Image data of a three-dimensional image is image data made by assigning pixel values to each of a plurality of voxels arranged three-dimensionally. This image data is referred to as volume data, voxel data, or the like. For displaying an image based on volume data, the image processor 230 executes a rendering process (such as volume rendering and MIP (Maximum Intensity Projection)) on this volume data and form image data of a pseudo three-dimensional image taken from a specified viewing direction. On a display device such as the display 207, the pseudo three-dimensional image based on the image data is displayed.

Further, the image processor 230 can also form stack data of a plurality of tomographic images. Stack data is image data obtained by arranging a plurality of tomographic images obtained along a plurality of scanning lines, based on the positional relation of the scanning lines.

The image processor 230 is provided with an image analyzer 231. The image analyzer 231 analyzes an image of the fundus oculi Ef. An example of a process executed by the image analyzer 231 will be described below.

When a still image and a motion image of the fundus oculi Ef are obtained, the image analyzer 231 specifies an image region in the motion image corresponding to a region of interest in the still image. A still image is, for example, a color image, fluorescent image, or tomographic image of the fundus oculi Ef. A motion image is, for example, a motion image of the fundus oculi Ef obtained by using an illumination light of near-infrared region or visible region.

Generally, a motion image is composed of still images (frame images) acquired sequentially at a predetermined time interval (frame rate). Specification of an image region in a motion image is executed by specifying an image region corresponding to a region of interest in a still image, for frame images composing the motion image.

In the fundus oculi observation device 1 according to the present embodiment, an optical system for acquiring a still image and an optical system for acquiring a motion image have some parts in common. To be precise, a still image and a motion image are respectively acquired by using a light emitted from one of the light sources 101, 103 and 160. All of the lights emitted from the light sources 101, 103 and 160 are applied to the eye E by an optical system including the objective lens 113, and all of the fundus oculi reflected lights are detected via an optical system including the objective lens 113.

By adopting such a configuration, it is possible to previously link a position in a still image with a position in a motion image. This link information is previously stored in, for example, the storage 212. The image analyzer 231 specifies an image region in a motion image corresponding to a region of interest in a still image by referring to the link information.

The method for specifying an image region is not limited to the above. For example, it is possible to analyze a still image and a motion image to specify an image region. As one example, it is possible to extract an image region having a similar shape to a region of interest, from a motion image, by a correlation process of determining the correlation between images, and use it as a target image region.

Further, it is possible to analyze a still image, and specify the distance and direction from a characteristic point of the fundus oculi Ef (center of the papilla, fovea centralis, bifurcation position of blood vessels, etc.) to a region of interest, and also specify an image region in a motion image based on the position of the characteristic point in the motion image and the specified distance and direction.

Other processes executed by the image analyzer 231 will be described later.

The image processor 230 includes the microprocessor 201, the RAM 202, the ROM 203, the hard disk drive 204 (the control program 204*a*), and so on. The image analyzer 231 includes the microprocessor 201, and so on. The image analyzer 231 is an example of the "specifying part" of the present invention. The specifying part may include the display 240A (image display) and the manipulation part 240B (designating part).

(User Interface)

The user interface 240 (UI) is provided with the display 240A and the manipulation part 240B. The display 240A is configured by a display device such as the display 207. In particular, the display 240A displays a motion image of the fundus oculi Ef, as an example of the "display" of the present invention.

The manipulation part 240B is configured by an input device and an operation device, such as a keyboard 205 and a mouse 206. In particular, the manipulation part 240B is used as the "manipulation part" of the present invention.

[Scan with Signal Light and Image Processing]

A scan with the signal light LS and image processing will be described with reference to FIGS. 9~12. The scanning lines shown in these figures are not actually set on the fundus oculi Ef, and are virtual lines representing the path of the application position of signal light LS. Moreover, each of the scanning lines also means a line representing a cross-section position of a tomographic image.

A scan with the signal light LS is performed by changing the directions of the reflecting surfaces of the Galvano mirrors 141A and 141B of the scan unit 141 as described above. The controller 210 controls the mirror drive mechanisms 241 and 242, respectively, to change the directions of the reflecting surfaces of the Galvano mirrors 141A and 141B, thereby scanning the fundus oculi Ef with the signal light LS.

When the facing direction of the reflecting surface of the Galvano mirror 141A is changed, a scan of the fundus oculi Ef with the signal light LS is performed in the horizontal direction (x-direction in FIG. 1). On the other hand, when the facing direction of the reflecting surface of the Galvano mirror 141B is changed, a scan of the fundus oculi Ef with the signal light LS is performed in the vertical direction (y-direction in FIG. 1). Further, by changing the facing directions of the reflecting surfaces of both the Galvano mirrors 141A and 141B simultaneously, it is possible to scan with the signal light LS in the composite direction of the x-direction and y-direction. That is to say, by controlling the two Galvano mirrors 141A and 141B, it is possible to scan with the signal light LS in any direction on the x-y plane.

FIGS. 9A and 9B show an example of a scanning pattern of the signal light LS for forming an image of the fundus oculi Ef. FIG. 9A shows an example of a scanning pattern of the signal light LS when the fundus oculi Ef is seen from a direction that the signal light LS enters the eye E (that is, seen from −z side toward +z side in FIG. 1). Further, FIG. 9B shows an example of an arrangement pattern of the scanning points (positions to execute image measurement) on each scanning line on the fundus oculi Ef.

As shown in FIG. 9A, a scan with the signal light LS is performed in a preset rectangular scanning region R. In the scanning region R, a plurality of (m lines of) scanning lines R1~Rm are set in the x-direction. When a scan with the signal light LS is performed along the respective scanning lines Ri (i=1~m), detection signals of the interference light LC are generated.

A direction of each scanning line Ri will be referred to as the "main scanning direction" and a direction orthogonal thereto will be referred to as the "sub-scanning direction." Accordingly, a scan in the main scanning direction of the signal light LS is executed by changing the facing direction of the reflecting surface of the Galvano mirror 141A. On the other hand, a scan in the sub-scanning direction is executed by changing the facing direction of the reflecting surface of the Galvano mirror 141B.

On each scanning line Ri, as shown in FIG. 9B, a plurality of (n pieces of) scanning points Ri1~Rin are preset.

In order to execute the scan shown in FIGS. 9A and 9B, the controller 210 firstly controls the Galvano mirrors 141A and 141B to set an entrance target of the signal light LS into the fundus oculi Ef to a scan start position RS (scanning point R11) on the first scanning line R1. Subsequently, the controller 210 controls the low-coherence light source 160 to flush the low-coherence light L0, thereby making the signal light LS enter the scan start position RS. The CCD 184 receives the interference light LC based on the fundus oculi reflected light of this signal light LS at the scan start position RS, and outputs the detection signal to the controller 210.

Next, the controller 210 controls the Galvano mirror 141A to scan with the signal light LS in the main scanning direction and set the incident target to a scanning point R12, and makes the low-coherence light L0 flushed to make the signal light LS enter into the scanning point R12. The CCD 184 receives the interference light LC based on the fundus oculi reflected light of this signal light LS at the scanning point R12, and then outputs the detection signal to the controller 210.

Likewise, the controller 210 acquires detection signals outputted from the CCD 184 in accordance with the interference light LC for each scanning point, by flushing the low-coherence light L0 at each scanning point while sequentially moving the incident target of the signal light LS from a scanning point R13, R14, - - - , R1(n−1), and R1n in order.

When the measurement at the last scanning point R1n on the first scanning line R1 is finished, the controller 210 controls the Galvano mirrors 141A and 141B simultaneously to move the incident target of the signal light LS to the first scanning point R21 on the second scanning line R2 following a line switching scan r. Then, by conducting the previously described measurement on each scanning point R2j (j=1 through n) on this second scanning line R2, detection signals corresponding to the respective scanning points R2*j* are acquired.

Likewise, the measurement is conducted on the third scanning line R3, - - -, the m−1th scanning line R(m−1), the mth scanning line Rm to acquire the detection signals corresponding to the respective scanning points. Symbol RE on the scanning line Rm is a scan end position corresponding to a scanning point Rmn.

Thus, the controller 210 acquires m×n pieces of detection signals corresponding to m×n pieces of scanning points Rij (i=1~m, j=1~n) in the scanning region R. Hereinafter, the detection signal corresponding to the scanning point Rij may be represented by Dij.

Such interlocking control of the movement of the scanning points and the emission of the low-coherence light L0 can be realized by, for example, synchronizing timing for transmission of control signals to the mirror drive mechanisms 241 and 242 and timing for transmission of a control signal to the low-coherence light source 160.

When each of the Galvano mirrors 141A and 141 B is operated as described above, the controller 210 stores the position of the scanning line Ri and the position of the scanning point Rij (coordinates on the x-y coordinate system) as information representing the content of the operation. This stored content (scan position information) is used in an image forming process as conventional.

Next, an example of the image processing in the case of executing the scan with the signal light LS shown in FIG. 9 will be described.

The image forming part 220 forms tomographic images of the fundus oculi Ef along the respective scanning lines Ri (the main scanning direction). Further, the image processor 230 forms a three-dimensional image of the fundus oculi Ef based on the tomographic images formed by the image forming part 220.

The process of forming tomographic images by the image forming part 220 includes two steps of arithmetic processes as conventional. In the first step of arithmetic process, based on the detection signal Dij corresponding to each scanning point Rij, an image in the depth direction (z-direction shown in FIG. 1) of the fundus oculi Ef at the scanning point Rij is formed.

FIG. 10 shows a pattern of a tomographic image formed by the image forming part 220 when a scan with the signal light LS is executed as shown in FIG. 9. In the second step of arithmetic process, for each scanning line Ri, based on the depthwise images at the n pieces of scanning points Ri1~Rin on the scanning line Ri, a tomographic image Gi of the fundus oculi Ef along the scanning line Ri is formed. In this case, the image forming part 220 determines the arrangement and interval of the scanning points Ri1~Rin with reference to the positional information of the scanning points Ri1~Rin (the aforementioned scan position information), and forms the scanning line Ri. Through the above process, m pieces of tomographic images G1~Gm at different positions in the sub-scanning direction (y-direction) are obtained.

Next, the process of forming a three-dimensional image of the fundus oculi Ef by the image processor 230 will be described. A three-dimensional image of the fundus oculi Ef is formed based on the m pieces of tomographic images obtained through the above arithmetic process. The image processor 230 forms a three-dimensional image of the fundus oculi Ef by executing a known interpolating process of interpolating an image between the adjacent tomographic images Gi and G(i+1).

In this case, the image processor 230 determines the arrangement and interval of the respective scanning lines Ri while referring to the positional information of each scanning line Ri to form the three-dimensional image. In this three-dimensional image, a three-dimensional coordinate system (x, y, z) is set based on the positional information of each scanning point Rij (the aforementioned scan position information) and the z-coordinate in the depthwise image.

Further, based on this three-dimensional image, the image processor 230 can form a tomographic image of the fundus oculi Ef in a cross-section in any direction other than the main scanning direction (x-direction). When the cross-section is designated, the image processor 230 specifies the position of each scanning point (and/or the interpolated depthwise image) on this designated cross-section, extracts the depthwise image at each determined position (and/or an interpolated depthwise image), and arranges the plurality of extracted depthwise images, thereby forming a tomographic image of the fundus oculi Ef in the designated cross-section.

An image Gmj shown in FIG. 10 represents an image in the depth direction (z-direction) at the scanning point Rmj on the scanning line Rm. Likewise, a depthwise image at each scanning point Rij on each scanning line Ri, formed in the aforementioned first-step of arithmetic process is referred to as an "image Gij."

FIG. 11 shows another scanning pattern of the signal light LS. FIG. 11 is a view when the fundus oculi Ef is seen from a direction in which the signal light LS enters the eye E.

In the scanning pattern shown in FIG. 11, a scan with the signal light LS is executed in a circular scanning region T. The shape of the scanning region is not limited to a circle and may be, for example, an arbitrary shape such as ellipse.

Within the scanning region T, a plurality of (m lines of) scanning lines T1~Tm are set, which are arranged radially. Respective scanning lines Ti are set so as to cross at a predetermined position C (central position). When a scan with the signal light LS is executed along each scanning line Ti, a detection signal of the interference light LC is generated. Each scanning line Ti (i=1~m) is set by a scan setting part 213. The operator may operate the manipulation part 240B to set the scanning line Ti at a desired position. This setting operation can be performed, for example, using the mouse 206.

On each scanning line Ti, a plurality of scanning points Ti1~Tin (not shown) are set as in FIG. 9B. Symbol TS represents a scan start position in this scanning pattern, and symbol TE represents a scan end position.

According to the scanning pattern shown in FIG. 11, m pieces of tomographic images are obtained, which are radially arranged and whose cross sections are the respective scanning lines Ti. Moreover, it is possible to form a three-dimensional image based on these m pieces of tomographic images. In this scanning pattern, the density of the scanning lines Ti is high in the vicinity of the central position C and the density of the scanning lines Ti is low at an area far from the central position C. Therefore, a three-dimensional image of only the vicinity of the central position C may be formed considering the accuracy of the three-dimensional image.

FIG. 12 shows another scanning pattern of the signal light LS. FIG. 12 is a view when the fundus oculi Ef is seen from a direction in which the signal light LS enters the eye E.

In the scanning pattern shown in FIG. 12, a scan with the signal light LS is executed in a circular scanning region U. The shape of the scanning region is not limited to a circle, and may be, for example, an arbitrary shape such as ellipse.

Within the scanning region U, a plurality of scanning lines U1~U6 (in this case, six lines) are set, which are concentrically arranged. Each scanning line Ui (i=1~6) is set so as to be centered around a predetermined position D (central position). When a scan with the signal light LS is executed along each scanning line Ui, a detection signal of the interference light LC is generated. Each scanning line Ui is set by the scan setting part 213. The operator may operate the manipulation part 240B to set the scanning line Ui at a desired position. This setting operation can be performed, for example, using the mouse 206.

On each scanning line Ui, as in FIG. 9B, a plurality of scanning points Ui1~Uin (not shown) are set.

According to the scanning pattern shown in FIG. 12, six tomographic images are obtained, which are arranged concentrically and whose cross-sections are the respective scanning lines Ui. Moreover, it is possible to form a three-dimensional image based on the six tomographic images.

In the description with FIG. 12, six concentric scanning lines are set, but the number of the concentric scanning lines can be set arbitrarily. In particular, in the case of forming a three-dimensional image, it is desired to set many scanning lines so that the interval of the scanning lines is sufficiently narrow. There is no need to set a plurality of circular scanning lines, and may be one line.

The scanning patterns of the signal light LS are not limited to the above. For example, it is possible to scan with the signal light LS only in the horizontal direction (x direction), scan only in the vertical direction (y direction), scan in the form of a cross with one line each in both horizontal and vertical directions, or scan helically.

Further, it is also possible to apply a combination of two or more scanning patterns. For example, it is possible to combine the radial scanning pattern of FIG. 11 and the concentric scanning pattern of FIG. 12. In this case, it is possible to make the scanning regions T and U and central positions C and D coincide with each other.

In other words, as described above, the scan unit 141 is configured so as to be capable of scanning with the signal light LS independently in the x direction and y direction, so it is possible to scan with the signal light LS along an arbitrary trajectory on the x-y plane.

[Usage Patterns]

Usage patterns of the fundus oculi observation device 1 will be described.

[First Usage Pattern]

In a first usage pattern, a case of using a color image as a still image of the fundus oculi Ef and using a near-infrared image as a motion image will be described. A flowchart shown in FIG. 13 shows an example of the present usage pattern.

First, the magnification calculator 214 calculates the photographing magnification considering the magnification of the ocular optical system of the eye E, based on optical information of the eye E (S1). In a case that the optical information was measured in the past, the operator can input the optical information by using the user interface 240. Moreover, in a case that the measurement result of the optical information is stored in a database, the controller 210 may access the database and automatically acquire the optical information. The magnification calculator 214 calculates the photographing magnification based on the optical information inputted in this manner. The calculated photographing magnification is stored into the storage 212 by the main controller 211.

Next, a motion image of the fundus oculi Ef by near-infrared light (a near-infrared motion image) is displayed on display 240A (S2), and alignment for capturing a color image is performed (S3).

For this purpose, the operator first operates the manipulation part 240B to request start of the alignment. The main controller 211 having received this request controls the imaging light source 103 and the imaging device 10 to acquire a near-infrared motion image. The main controller 211 controls the display 240A to display the acquired near-infrared motion image in real time.

Further, the main controller 211 controls the alignment light source 190a to turn on to project alignment bright points P1 and P2 on the fundus oculi Ef, and also controls the display 240A to display the scale S. The operator performs the above-mentioned alignment operation to adjust the positional relation of the optical systems 100 and 120 with the eye E.

When the alignment is completed, a color image of the fundus oculi Ef is captured (S4). The capture of the color image is executed when the operator operates the manipulation part 240B to request the capture and the main controller 211 having received the request controls the observation light source 101 and the imaging device 12. The main controller 211 controls the display 240A to display the captured color image (S5). Even on and after the capture of the color image, it is possible to continuously acquire and display the near-infrared motion images.

FIG. 14 shows an example of a pattern of displaying a color image and a near-infrared motion image when an attention site in the fundus oculi Ef is the optic papilla. The display 240A is provided with a still image display 2410 and a motion image display 2420. The main controller 211 controls the still image display 2410 to display a color image H' captured in Step 4. Moreover, the controller 211 controls the motion image display 2420 to display a near-infrared motion image H continuously acquired from the time point of Step 2.

The near-infrared motion image is displayed while updating, at a predetermined frame rate, a frame image acquired at a predetermined time interval. Besides, the alignment bright points P1 and P2 and the scale S, which are not shown in the drawing, are displayed together with the near-infrared motion image on the motion image display 2420. A usage pattern when the display pattern of FIG. 14 is applied will be described below.

The operator operates the manipulation part 240B to designate an image region (a region of interest Q') corresponding to the optic papilla in the color image H' (S6).

An example of this designation operation will be described. First, the operator observes the color image H' and grasps an image region corresponding to the optic papilla. Then the operator designates a plurality of positions p on the edge of this image region by a clicking operation or the like (refer to FIG. 15).

When the plurality of positions p in the color image H' are designated, the image analyzer 231 determines the region of interest Q' based on these positions p (S7). As a method for determining this region of interest Q', it is possible to apply, for example, a method of obtaining a circle or ellipse passing through the plurality of positions p, a method of obtaining a circle or ellipse that approximates a diagram passing through the plurality of positions p, and a method of obtaining an approximation curve (Bezier curve, spline curve or the like) based on the plurality of positions p.

Thus, in this embodiment, the region of interest Q' in the color image H' is not determined at first, and an image region determined based on an image region that the operator recognizes as representing the optic papilla is treated as the region of interest Q'.

Further, the image analyzer 231 specifies a central position q' of the region of interest Q' determined in step 7, namely, a position q' corresponding to the center of the optic papilla (S8). As the central position q': when the region of interest Q' is formed in to a circle, it is possible to apply the center of the circle; when the region of interest Q' is formed into an ellipse, it is possible to apply a position where the long axis and the short axis cross (or an intermediate position between the two foci); and when the region of interest Q' is formed into an arbitrary shape, it is possible to apply the gravity center of the shape, or the like. Thus, in Step 8, a characteristic position of the region of interest Q', which can be considered to be the center of the optic papilla, is properly specified as the central position q'.

Next, the image analyzer 231 specifies a position q (referred to as the reference position) in the near-infrared motion image H corresponding to the central position q' of the region of interest Q' (S9). The process of specifying an image region corresponding to the reference position q is described above.

The main controller 211 stores the coordinates (x-coordinate value and y-coordinate value) of the reference position q, and a frame image in which the reference position q has been specified, into the storage 212. This frame image is referred to as a reference image. The reference image may be the whole frame image, or may be part of the frame image. In the latter case, it is possible to, for example, extract only an image region corresponding to the inside of a frame-shaped image described below and set the image region as the reference image.

The reference position q represents a position corresponding to the center of the optic papilla in the near-infrared motion image H. Moreover, as shown in FIG. 16, the reference position q is positioned at almost the center of the image region Q (also refer to FIG. 14) corresponding to the optic papilla.

Subsequently, the main controller 211 controls the motion image display 2420 to display a frame-shaped image for adjusting the fixation position of the eye E (S10).

FIG. 16 shows an example of a pattern of displaying the frame-shaped image. A frame-shaped image W shown in FIG. 16 is an image representing a rectangular frame. The frame-shaped image W is displayed at a predetermined position in the motion image display 2420. In this usage pattern, the frame-shaped image W is displayed so that the center thereof coincides with the center of the motion image display 2420.

The display size of the frame-shaped image W may be a size corresponding to the scanning region of the signal light LS, or may be an arbitrary size that is larger than the image region Q corresponding to the optic papilla.

The shape and display size of the frame-shaped image are not limited to the above, and it is possible to properly employ an arbitrary shape and display size. The size of the frame-shaped image is previously set based on various factors having influences on the display size of the region of interest, such as the type of the attention site and the photographing magnification.

The operator operates the manipulation part 240B while observing the near-infrared motion image H, and adjusts a position to present the internal fixation target so that the image region Q corresponding to the optic papilla is positioned within the frame-shaped image W (S11). In this case, alignment with the alignment target is performed, as required.

When the image region Q is displayed within the frame-shaped image W, the operator operates the manipulation part 240B to request measurement of the OCT image (S12).

The controller 211 having received the request reads out the coordinates values of the reference position q and the reference image from the storage 212 to send to the image analyzer 231, and also sends a newly acquired frame image to the image analyzer 231. The image analyzer 231 executes position matching between the reference image and the new frame image (S13). Such position matching between images can be executed by, for example, a matching process considering the correlation between the images.

Further, the image analyzer 231 specifies a position in the new frame image corresponding to the reference position q, based on the coordinate values of the reference position q (S14). This specified position is referred to as a corresponding position. The main controller 211 sends the coordinate values of the corresponding position to the scan setting part 213.

The scan setting part 213 sets a scanning pattern of the signal light LS based on the coordinate values of the corresponding position and the photographing magnification obtained in Step 1 (S15). The photographing magnification is used to determine the size of the scanning region, the length of the scanning line, the interval between the scanning lines, the interval between the scanning points, and so on.

An example of setting the scanning pattern is shown in FIG. 17. A scanning pattern V shown in FIG. 17 is a combination of the radial scanning pattern of FIG. 11 and the concentric scanning pattern of FIG. 12. The two scanning patterns are set, respectively, so that the central positions C and D in the respective scanning patterns coincide with the abovementioned corresponding position.

The main controller 211 controls the low-coherence light source 160 and the mirror drive mechanisms 241 and 242 to scan the fundus oculi Ef with the signal light LS based on the scanning pattern set in Step 15 (S16).

The image forming part 220 successively forms tomographic images according to this scanning pattern, based on the detection signals sequentially inputted from the CCD 184 (S17). The main controller 211 controls the display 240A to display the formed tomographic images (S18). In this case, the tomographic images may be displayed together with the color image and the near-infrared motion image, or only the tomographic images may be displayed.

The main controller 211 stores the tomographic images into the storage 212. The image processor 230 forms a three-dimensional image based on the tomographic images, as necessary.

Further, the image analyzer 231 is capable of obtaining the layer thickness of the fundus oculi Ef by analyzing the acquired tomographic images and three-dimensional image. The layer of the fundus oculi Ef is, for example, the retina, the choroidea, and the sclera. Moreover the retina is composed of an internal limiting membrane, an optic nerve fiber layer, a ganglion cell layer, an inner plexiform layer, an inner granular layer, an outer plexiform layer, an outer granular layer, an external limiting membrane, a photoreceptor layer, a retinal pigment epithelium, and so on. As a method for obtaining the thicknesses of these layers, for example, it is possible to apply any conventional method such as the method described in Japanese Patent Application No. 2007-045831. Furthermore, the main controller 211 is capable of controlling so as to display a graph of the obtained layer thicknesses on the display 240A and so as to display the numeric values of the thicknesses.

Further, it is possible to configure so as to capture a near-infrared motion image when scanning with the signal light LS, calculate displacement between the frame image and a new frame image of step S13 and, when the displacement is larger than a predetermined threshold value, output alarm information such as a warning message. The alarm information indicates that the eye E has moved during the scan with the signal light LS. In a case that the alarm information is outputted, the operator can perform a re-measurement of the OCT image.

The abovementioned displacement calculation can be performed using an image matching process, or the like. Moreover, the abovementioned threshold value is set in advance. Furthermore, the alarm information may be visual information such as display of a message by the display 240A, or may be audible information such as a warning sound, or may be any other arbitrary perceptual information.

A case that the optic papilla is the attention site has been described above, but it is possible to execute the same process also in cases that the macula or a lesion site is the attention site. This is the end of the description of the first usage pattern.

[Second Usage Pattern]

In the first usage pattern, in order to determine a region of interest in a still image, the operator observes the still image and designates an image position. In a second usage pattern, a process of determining a region of interest is automated. FIG. 18 shows an example of the second usage pattern.

Steps 31~35 are executed in the same manner as Steps 1~5 of the first usage pattern (FIG. 13).

Next, the image analyzer 231 analyzes the color image H' and extracts a region of interest (S36). Further, the image analyzer 231 specifies the central position of this region of interest (S37).

The processes of Steps 36 and 37 will be described. The image analyzer 231 can extract a region of interest by, for example, analyzing the pixel values (luminance value, RGB value, and the like) of pixels forming the color image H'. This analysis process is performed based on preset pixel value information. The pixel value information is information representing the range of pixel values set according to the characteristics of the region of interest and, for example, is threshold value information of the pixel values for extracting the region of interest.

For example, in the case of extracting a region of interest corresponding to the optic papilla, considering a characteristic that the region of interest is brighter than the surroundings (for example, the luminance value is higher) and a characteristic that the shape is almost circular, it is possible to extract the region of interest by applying known image processing such as threshold processing and a border extraction process.

Furthermore, when the region of interest corresponding to the optic papilla is extracted, the image analyzer 231 specifies the center or gravity center of this region of interest as the central position.

In the case of extracting a region of interest corresponding to the macula, considering a characteristic that the region of interest is darker than the surroundings (for example, the luminance value is lower) and a characteristic that the shape is almost circular, it is possible to extract the region of interest by applying image processing as described above. When the region of interest corresponding to the macula is extracted, it is possible to specify the center or gravity center of this region of interest as the central position.

In the case of extracting a region of interest corresponding to a lesion site, by grasping how the lesion site is depicted in the color image H', namely, what characteristic of pixel values and shape the lesion site has when compared with the surroundings, it is possible to extract the region of interest by image processing as described above. The grasp of the depiction of the lesion site is possible by, for example, analyzing a fundus oculi image captured in the past and clinical data. Moreover, it is possible to obtain the central position in the same manner as mentioned above.

Further, in a case that a region of interest (for example, a lesion site) exists at a predetermined distance away from a characteristic point of the fundus oculi Ef such as the optic papilla and the macula, the image analyzer 231 first extracts an image region corresponding to the characteristic point in the same manner as mentioned above, and then specifies an image region at a predetermined distance away from a position (central position or the like) of this image region, thereby being capable of extracting the region of interest. A distance on an image can be calculated considering the photographing magnification obtained in Step 31, or the like.

The predetermined distance may be only a distance (scalar quantity), or may be a distance and direction (vector quantity). As the predetermined distance, for example, it is possible to use by reading out a distance that is obtained from a previously acquired image and is stored.

Steps 38~47 are respectively executed in the same manner as Steps 9~18 of the first usage pattern (FIG. 13). The image analyzer 231 in the second usage pattern functions as an example of the "extracting part" of the present invention. This is the end of the description of the second usage pattern.

[Action and Effect]

The action and effect of the aforementioned fundus oculi observation device 1 will be described.

The fundus oculi observation device 1 can form a motion image and a still image of the fundus oculi Ef. In the abovementioned usage patterns, the near-infrared motion image H is formed as the motion image, and the color image H' is formed as the still image. These images (particularly the still images) are stored into the storage 212.

Further, while a motion image is being formed, the fundus oculi observation device 1 specifies an image region in the motion image corresponding to a region of interest in a still image. Furthermore, by scanning with the signal light LS based on the specified image region, the fundus oculi observation device 1 forms tomographic images (OCT images) along those scanning lines. The region of interest means an image region corresponding to a predetermined attention site in the fundus oculi Ef.

According to the fundus oculi observation device 1, it is possible to determine a region of interest in a still image of relatively high image quality, specify an image region in a motion image corresponding to the region of interest, and set a measurement site (a scanning region) for a tomographic image. Accordingly, when compared with the conventional method of referring to only a motion image of relatively low image quality and set a measurement site, it is possible to certainly acquire an image of an attention site in the fundus oculi Ef.

Further, according to the fundus oculi observation device 1, it is possible to set a measurement site in a new frame image by using a certain frame image (reference image) in a motion image, so that it is possible to facilitate the alignment operation for acquiring an image of the attention site in the fundus oculi Ef.

Further, according to the abovementioned first usage pattern, a still image and a motion image are displayed, and the operator can specify an image region in the motion image corresponding to the region of interest designated in the still image, so that it is possible to acquire a tomographic image of a site desired by the operator.

In particular, in a case that an attention site (namely, a region of interest) has a predetermined shape, when the operator designates the region of interest, the fundus oculi observation device 1 obtains a characteristic position of the region of interest according to the predetermined shape, obtains a position in the motion image corresponding to the characteristic position, and scans with the signal light LS so as to pass through a position in the fundus oculi Ef corresponding to the position, thereby forming a tomographic image. Consequently, the operator can acquire a tomographic image of an appropriate measurement site only by designating a region of interest.

In a case that the attention site is the optic papilla or the macula, the predetermined shape is a substantially circular shape. A substantially circular shape is not only a circle and an ellipse, but also a curved line shape or polygonal shape similar to a circle and an ellipse. In a case that the attention site has a substantially circular shape, it is desirable to scan with the signal light LS along a plurality of scanning lines arranged radially, or to scan with the signal light LS along circular scanning lines having the center in common (refer to FIGS. 11 and 12). Besides, it is also possible to set a rectangular scanning region so as to include a substantially circular region of interest (refer to FIG. 9).

The shape of the region of interest is not limited to a substantially circular shape and may be, for example, an arbitrary shape such as a rectangle. Moreover, the region of interest is not limited to a two-dimensional image region. The region of interest may be a one-dimensional image region in the linear or curved form, or may be a zero-dimensional image region composed of a single point.

Further, according to the fundus oculi observation device 1, when determining a measurement site of a tomographic image, it is possible to display a frame-shaped image on a motion image, and change a position to project an internal fixation target on the fundus oculi Ef in response to the operator's operation to adjust the measurement site. In this case, the operator adjusts the fixation position of the eye E so that an image region corresponding to an attention site is positioned in the frame-shaped image. Furthermore, the fundus oculi observation device 1 is configured to, on the motion image after the adjustment, specifies an image region corresponding to a region of interest within a still image and executes a scan with the signal light LS. Therefore, compared with the conventional technology, it is possible to certainly acquire a tomographic image of an attention site in the fundus oculi Ef.

Further, according to the fundus oculi observation device 1, it is possible to project, to the fundus oculi Ef, an alignment target for adjusting the position of the optical system of the device with respect to the eye E, so that it is possible to facilitate the alignment operation. Moreover, it is possible to increase the certainty of acquisition of an image of an attention site.

Further, according to the fundus oculi observation device 1, it is possible to calculate the magnification of the ocular optical system of the eye E and scan with the signal light LS considering this magnification, so that it is possible to acquire an image of an attention site with more certainty and also acquire an image of higher accuracy.

[Modification]

The configuration described above is merely an example for favorably implementing the fundus oculi observation device relating to the present invention. Therefore, it is possible to properly apply any modification within the scope of the present invention.

First, by successively executing position matching with respect to a reference image on a frame image sequentially acquired as a motion image, it is possible to execute image position matching on the motion image in real time.

Further, although a still image is a color image and a motion image is a near-infrared motion image in the description of the above embodiment, the still image and the motion image are not limited to them. For example, it is possible to use a fluorescent image as the still image. A fluorescent image can depict fundus oculi blood vessels in detail, and therefore, is suitable in a case that a region of interest related to blood vessels (for example, neovascularization) is an observation target.

Further, it is possible to use a tomographic image as the motion image and still image (tomographic motion image and tomographic still image). In the case of using a tomographic motion image, considering a time taken for scan with a signal light, it is desirable to set a small number of scanning lines (for example, one line through several lines) and display the motion image in real time.

Position matching between tomographic images can be performed, for example, in the same manner as in the above-mentioned embodiment. Position matching between a two-dimensional image of the fundus oculi surface (color image or fluorescent image) and a tomographic image can be performed by associating the position (coordinate values) on the fundus oculi surface and the cross-section position of the tomographic image (scan position information). Moreover, for example, the position matching between the tomographic image and the two-dimensional image may be performed by using an accumulated image described in Japanese Patent Application No. 2006-160896. The accumulated image is an image obtained by accumulating a plurality of tomographic images in the depth direction, and is a two-dimensional image representing the fundus oculi surface.

Further, as in the abovementioned second usage pattern, it is possible to extract an attention site from a tomographic image of the fundus oculi Ef. In a case that the region of interest corresponds to the optic papilla or the macula, it is possible to extract the region of interest based on the shape of the site. For example, the optic papilla and the macula are concave in the inward direction (z-direction) of the fundus oculi Ef compared with the surrounding sites. The image analyzer 231 specifies an image region corresponding to the surface of the fundus oculi Ef, namely, the border between the retina and the vitreous body, by analyzing the pixel values of the tomographic image. Furthermore, the image analyzer 231 analyzes the shape of the specified image region to specify the region that is concave in the z-direction, and extracts the region as the region of interest.

A case that a region of interest is a lesion site will be described. A lesion site in a tomographic image includes one that can be specified by shape, such as retinal detachment, and one that is difficult to specify by shape, such as a tumor. The former one can be extracted in the same manner as the optic papilla or the like. On the other hand, in the latter one, the lesion site may be expressed by different pixel values from the surrounding sites (luminance value or the like). In this case, the image analyzer 231 can refer to the pixel values of the tomographic image to specify an image region corresponding to the lesion site, and extract the region of interest.

Further, although a still image of the fundus oculi is also acquired by the fundus oculi observation device in the abovementioned embodiment, the present invention is not limited to this configuration. For example, it is possible to store still images including color images, fluorescent images and tomographic images acquired by another device (retinal camera, optical image measurement device, or the like) into a storage, and read out the still images to use for position matching with a motion image.

Further, although the position of the reference mirror 174 is changed and the difference in optical path length between the optical path of the signal light LS and the optical path of the reference light LR is changed in the abovementioned embodiment, the method for changing the difference in optical path length is not limited to this. For example, by integrally moving the retinal camera unit 1A and the OCT unit 150 with respect to the eye E and changing the optical path length of the signal light LS, it is possible to change the difference in optical path length. Moreover, by moving a measurement object in the depth direction (z-direction), it is possible to change the difference in optical path length.

Further, although the fundus oculi observation device described in the abovementioned embodiment includes a Fourier-domain type optical image measurement device, it is possible to apply the configuration of the present invention to any type of device that scans the eye with a light beam, such as the Swept Source type and the Time-Domain type.

[Program]

A program according to the present invention will be described. The control program 204a in the above-mentioned embodiment is an example of the program according to the present invention.

The program according to the present invention is a program to control a fundus oculi observation device that has: a forming part for forming a motion image of the fundus oculi; an interference-light generator that splits a low-coherence light into a signal light and a reference light and superimposes the signal light propagated through the fundus oculi and the reference light propagated through a reference object to generate an interference light; a detector that detects the interference light; a scanner that scans the fundus oculi with a signal light; and a computer provided with a storage for storing still images of the fundus oculi. The arithmetic and control unit 200 in the abovementioned embodiment is an example of the computer.

More specifically, the program according to the present invention makes the computer function as the specifying part, controller and image forming part as described below. (1) Specifying part: When the motion image is formed by the forming part, it specifies an image region within the motion image corresponding to the region of interest within the still image. (2) Controller: It controls the scanner to scan with the signal light based on the specified image region. (3) Image forming part: It forms a tomographic image of the fundus oculi based on the result of detection of the interference light based on the signal light for scan by the scanner. The image forming part 220 in the abovementioned embodiment is an example of the image forming part.

According to the program, it is possible to realize a fundus oculi observation device as in the abovementioned embodiment, so that, compared with the conventional technology, it is possible to certainly acquire an image of an attention site in the fundus oculi. Moreover, the alignment operation for acquiring an image of the attention site in the fundus oculi can be facilitated.

In the program according to the present invention, it is possible to store into any storage medium that can be read by a computer drive device. For example, it is possible to use a storage medium such as an optical disc, a magneto-optical disc (CD-ROM/DVD-RAM/DVD-ROM/MO, or the like), a magnetic storage medium (hard disk/Floppy™) disks/ZIP, or the like). Moreover, it is also possible to store into a storage device such as a hard disk drive and a memory. Further, it is possible to transmit this program through a network such as the Internet and LAN.

BRIEF DESCRIPTION OF THE DRAWINGS

FIG. 9A shows an example of the scanning pattern the signal light when the fundus oculi is seen from the incident side of the signal light with respect to an eye. FIG. 9B shows an example of an arrangement pattern of scanning points on each scanning line.

Figure 1:
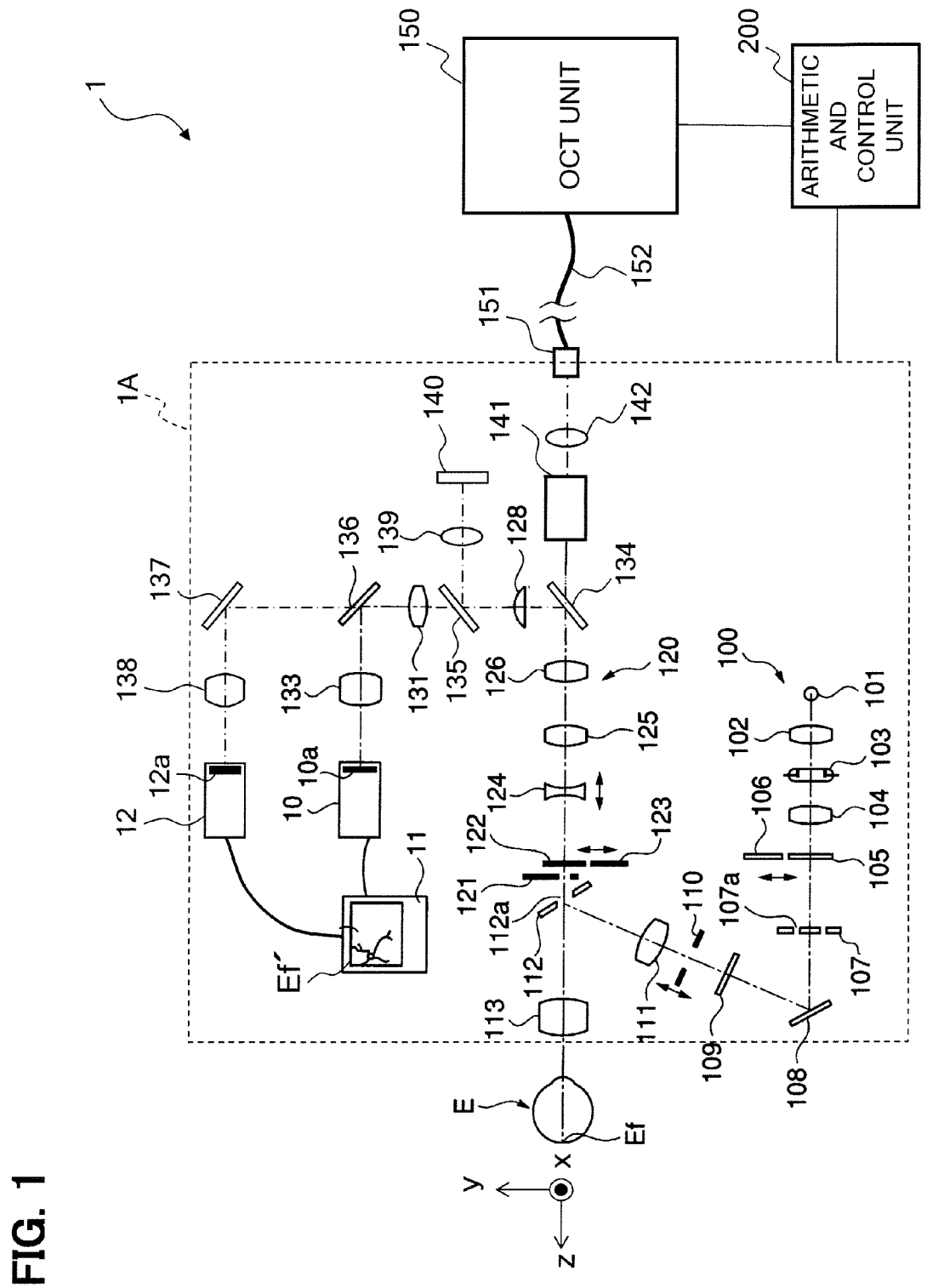
FIG. 1 is a schematic configuration diagram showing an example of the entire configuration in an embodiment of a fundus oculi observation device according to the present invention.
Figure 2A:
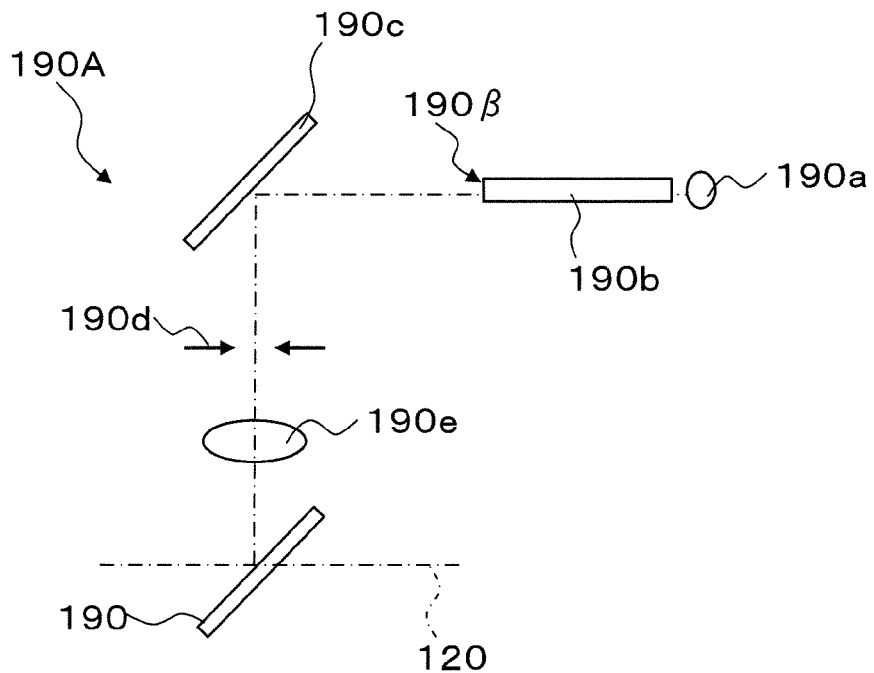
FIGS. 2A and 2B are schematic configuration diagrams showing an example of the configuration of an alignment optical system installed in a retinal camera unit in the embodiment of the fundus oculi observation device according to the present invention.
Figure 2B:
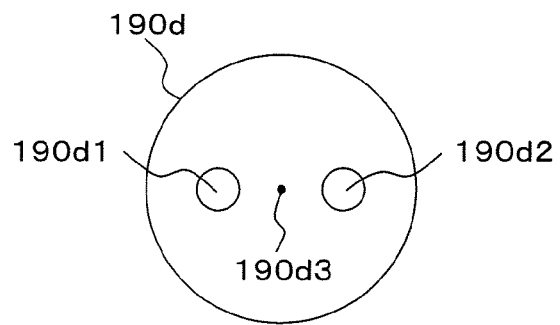
Figure 3A:
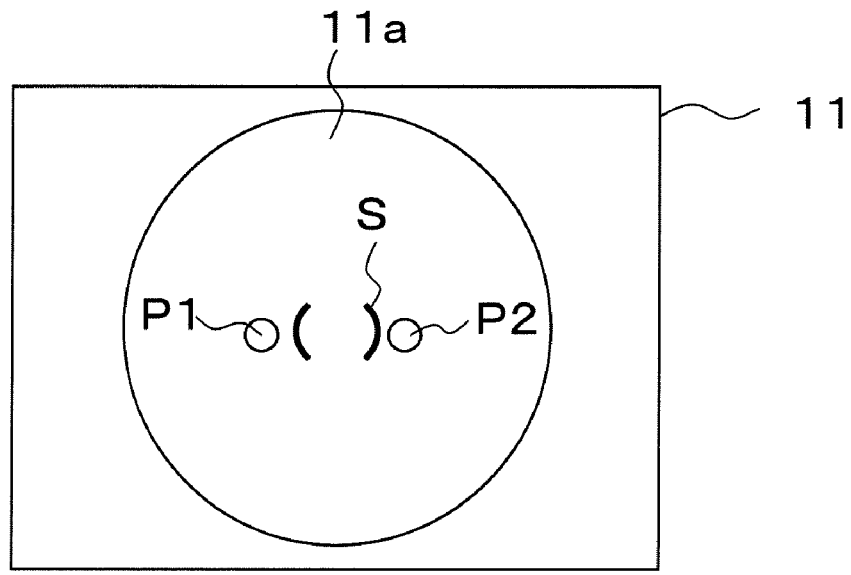
FIGS. 3A and 3B are schematic diagrams for explaining an example of an alignment operation in the embodiment of the fundus oculi observation device according to the present invention.
Figure 3B:
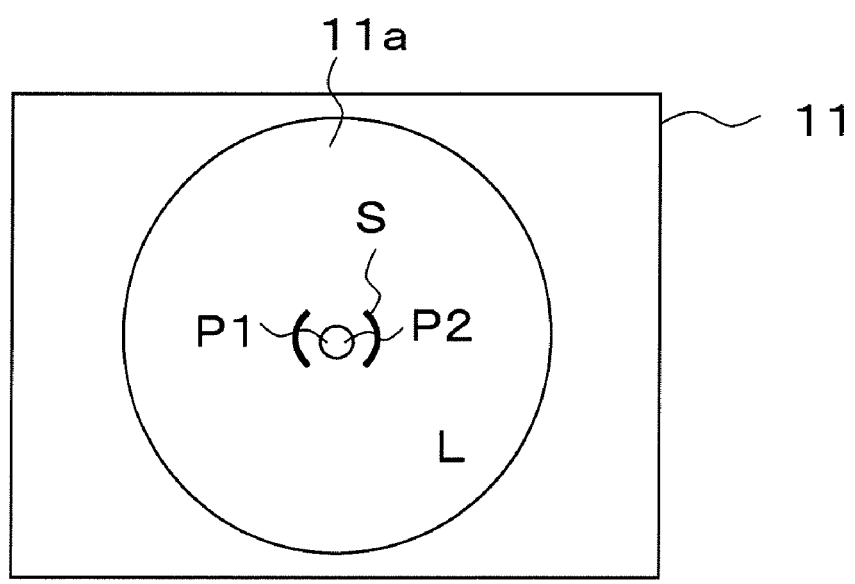
Figure 4:
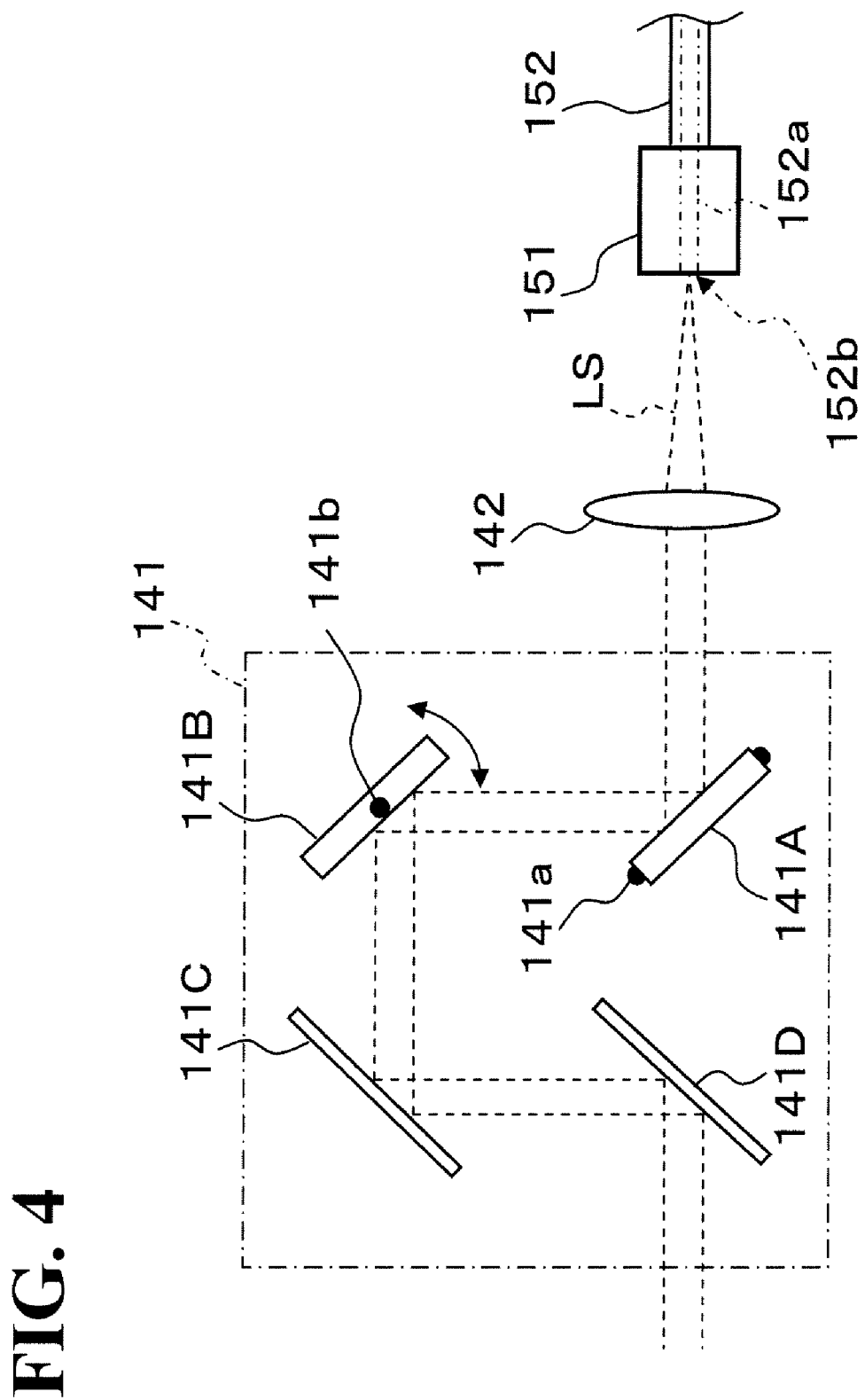
FIG. 4 is a schematic configuration diagram showing an example of the configuration of a scan unit installed in a retinal camera unit in the embodiment of the fundus oculi observation device according to the present invention.
Figure 5:
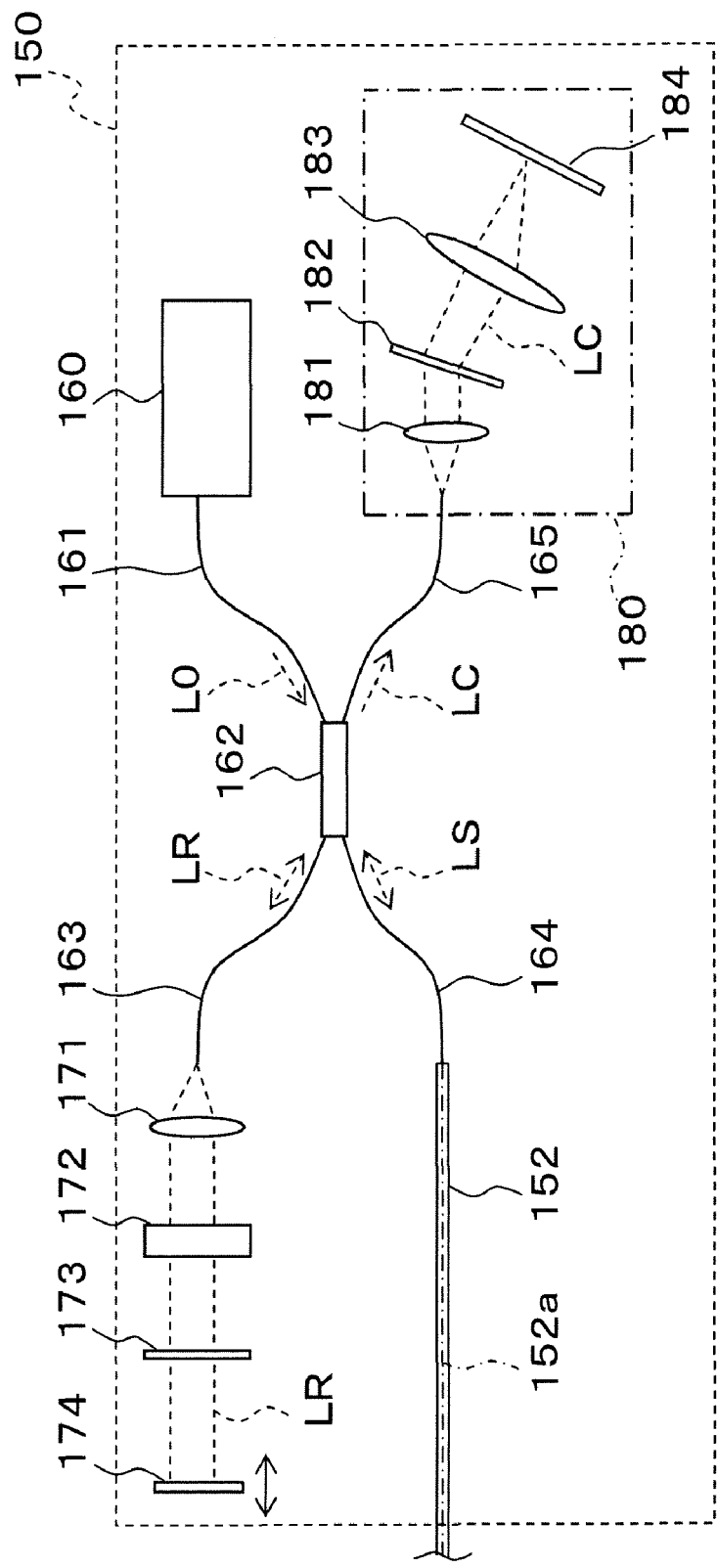
FIG. 5 is a schematic configuration diagram showing an example of the configuration of an OCT unit in the embodiment of the fundus oculi observation device according to the present invention.
Figure 6:
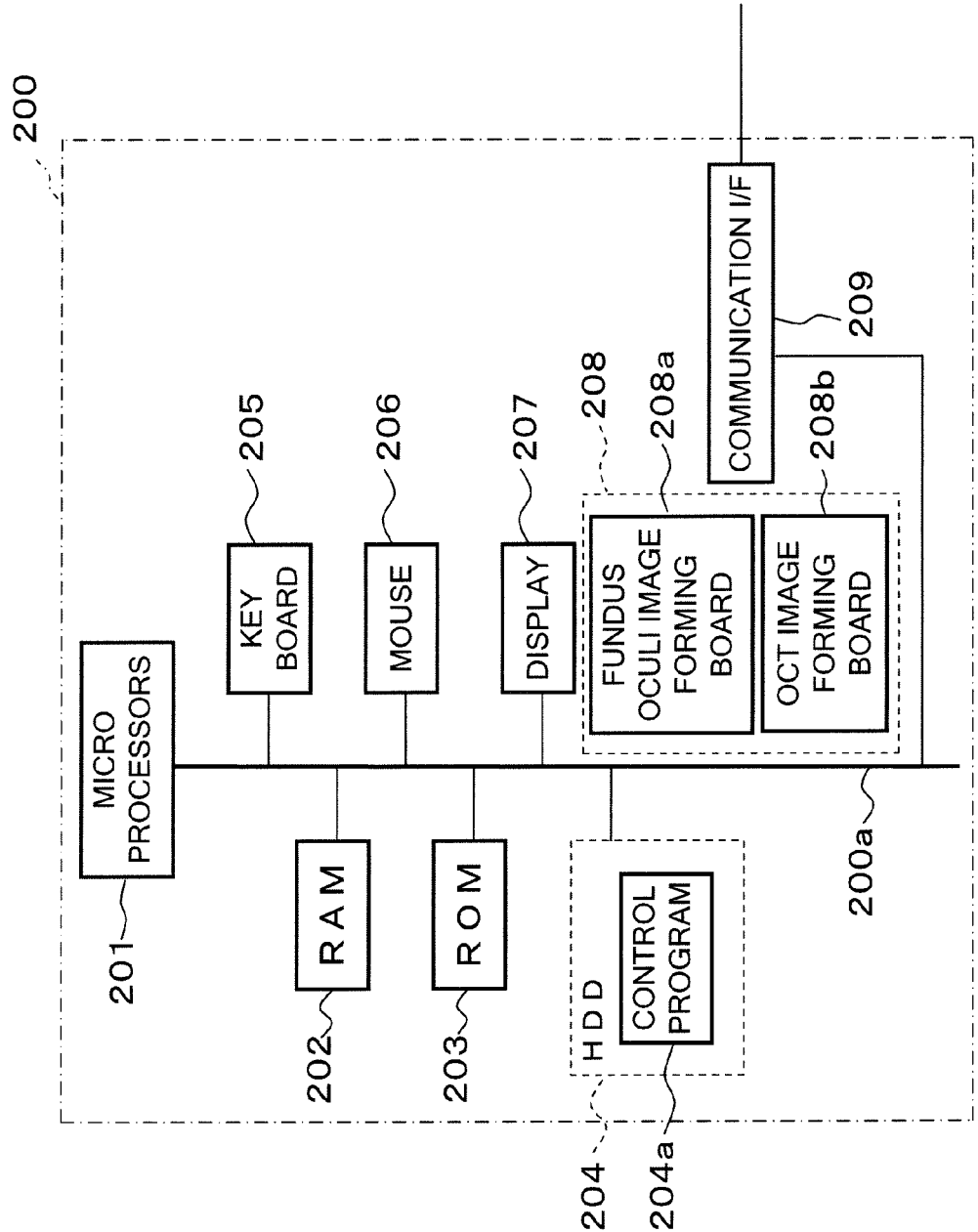
FIG. 6 is a schematic block diagram showing an example of the hardware configuration of an arithmetic and control unit in the embodiment of the fundus oculi observation device according to the present invention.
Figure 7:
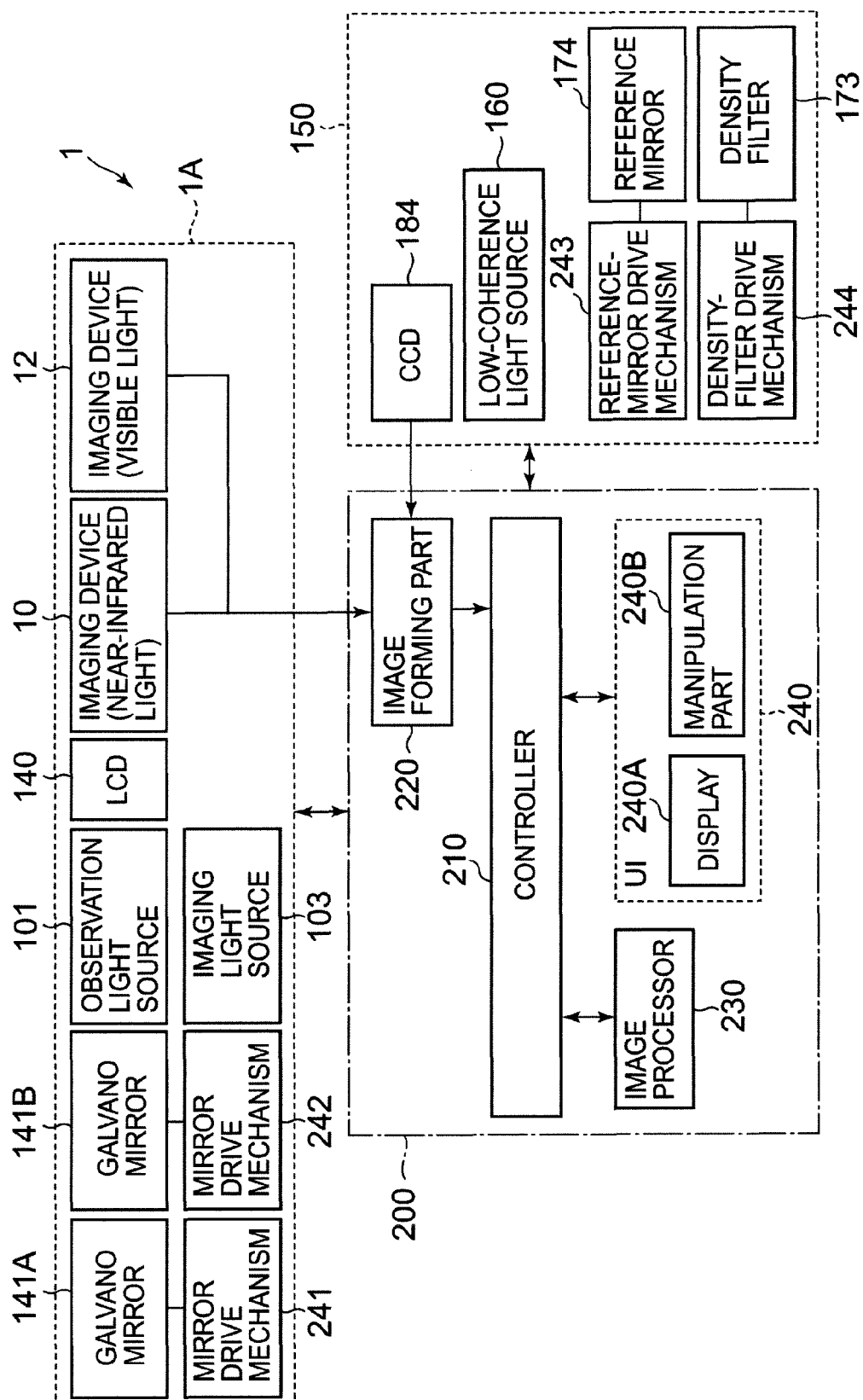
FIG. 7 is a schematic block diagram showing an example of the configuration of a control system in the embodiment of the fundus oculi observation device according to the present invention.
Figure 8:
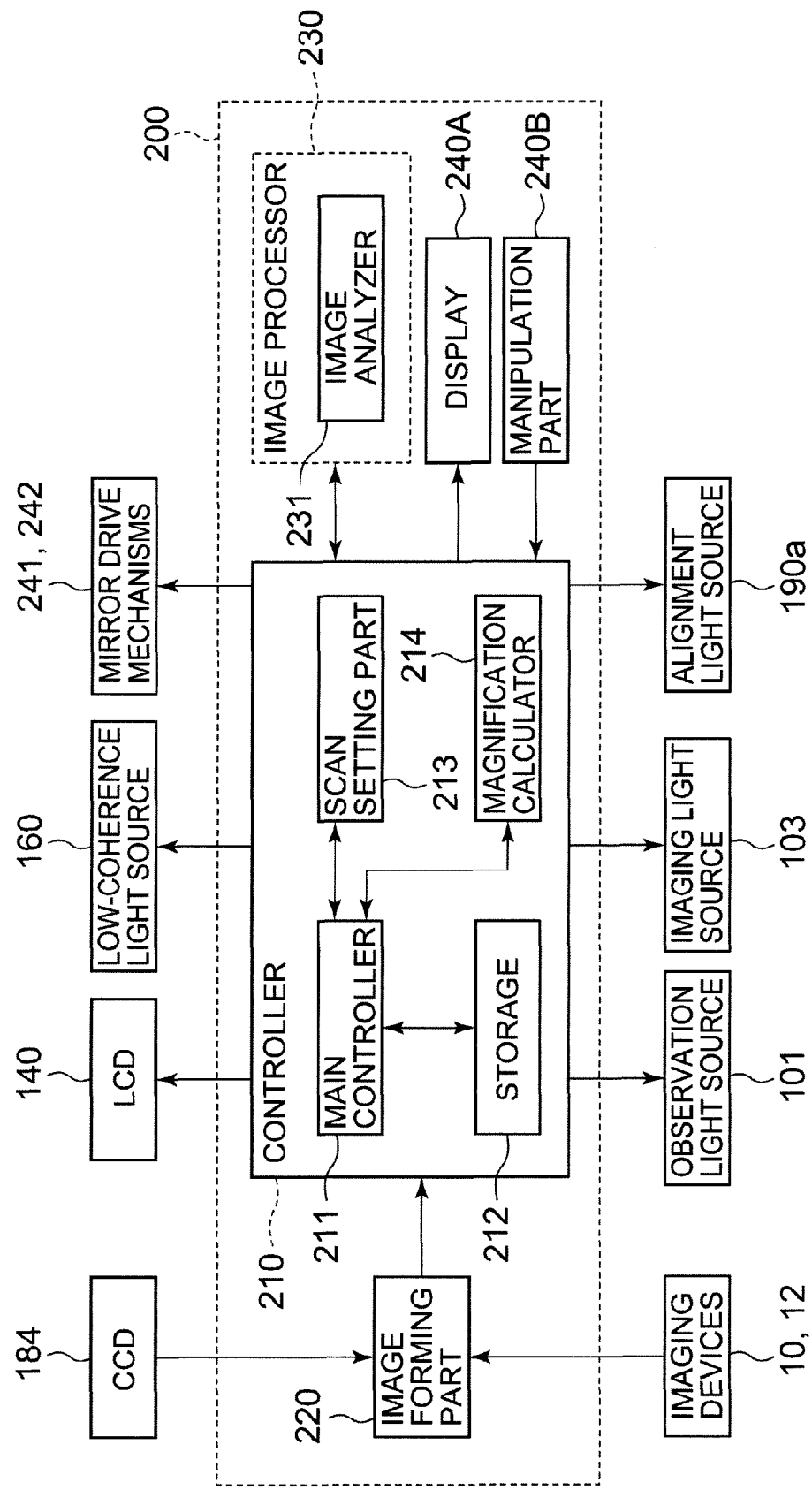
FIG. 8 is a schematic diagram showing an example of the configuration of the control system in the embodiment of the fundus oculi observation device according to the present invention.
Figure 9A:
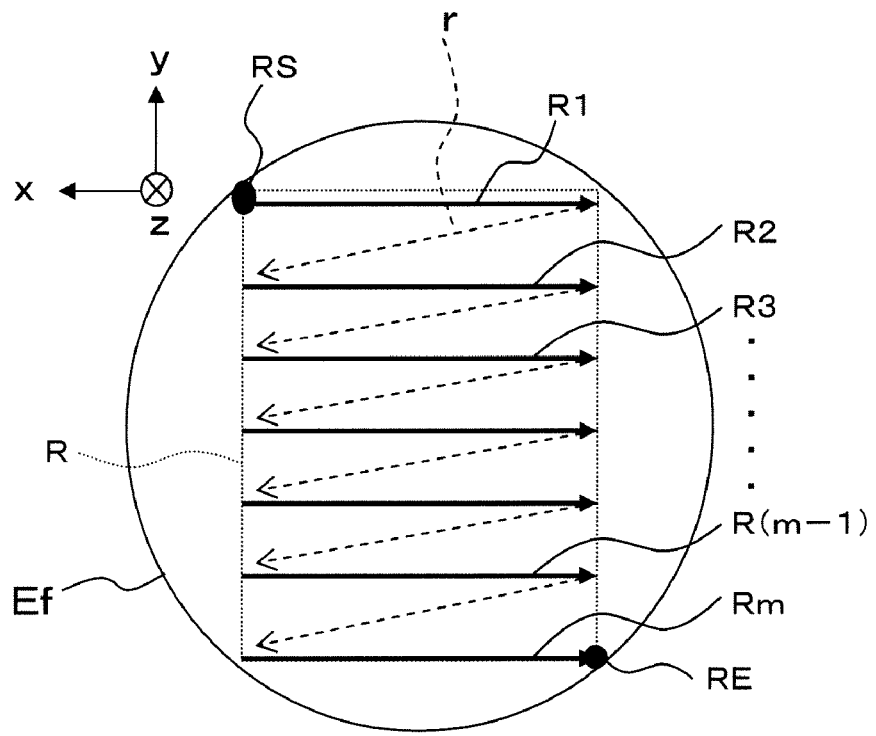
FIGS. 9A and 9B are schematic diagrams showing an example of a scanning pattern of a signal light in the embodiment of the fundus oculi observation device according to the present invention.
Figure 9B:
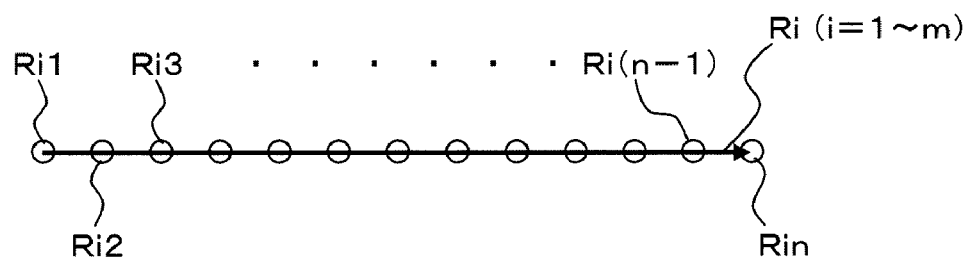
Figure 10:
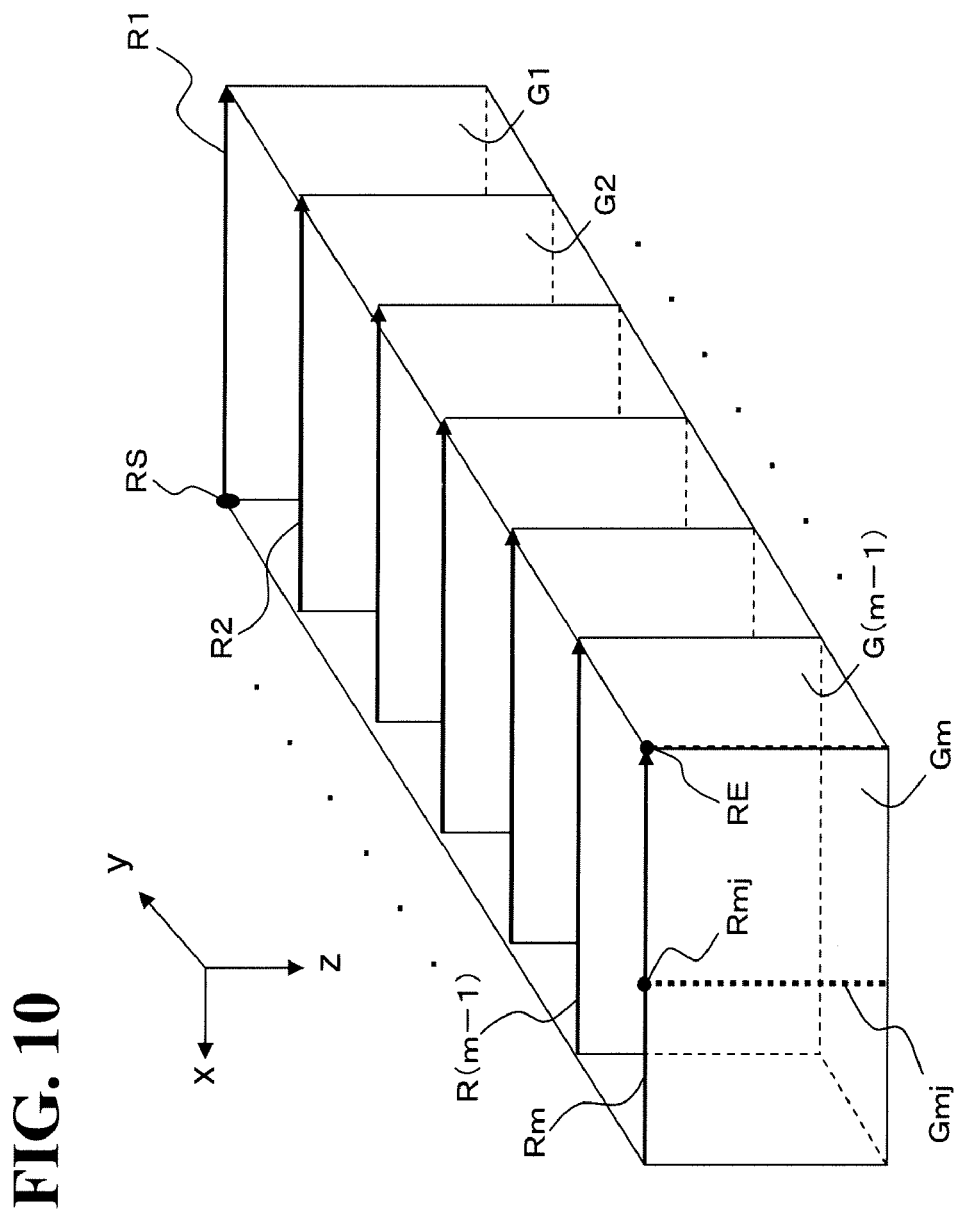
FIG. 10 is a schematic diagram showing an example of a scanning pattern of a signal light and a pattern of a tomographic image formed along each scanning line in the embodiment of the fundus oculi observation device according to the present invention.
Figure 11:
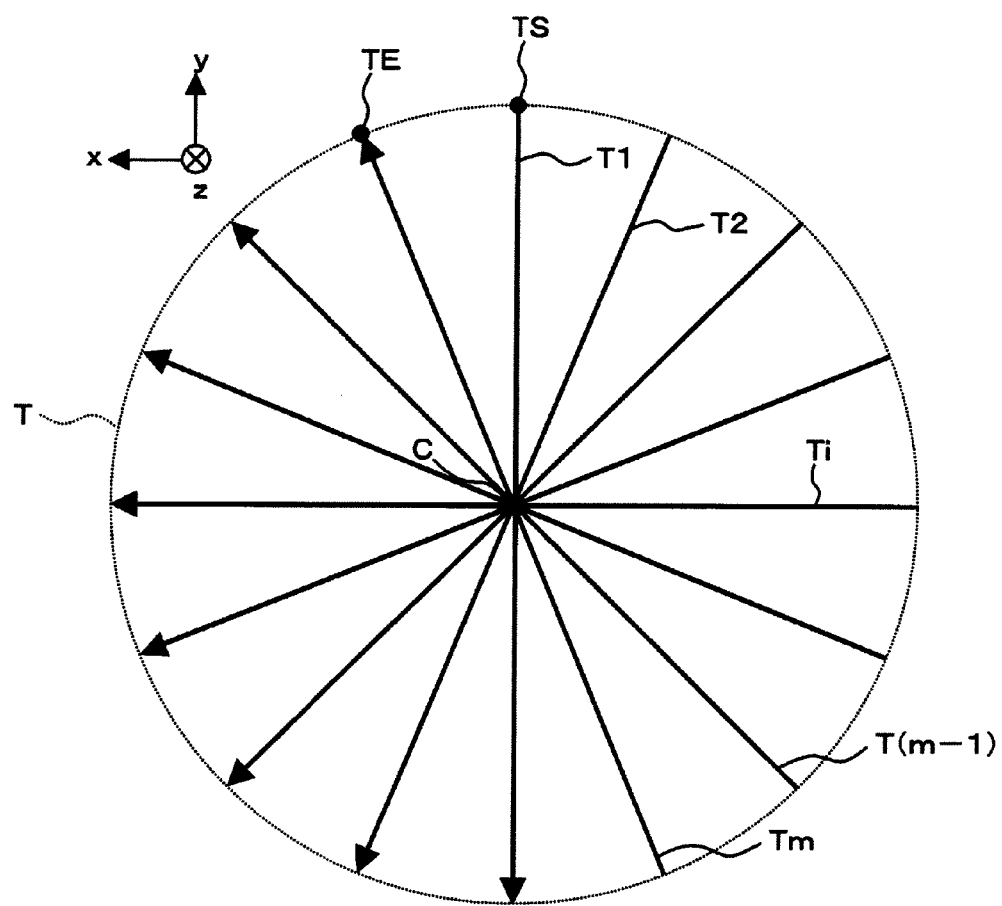
FIG. 11 is a schematic diagram showing an example of a scanning pattern of a signal light in the embodiment of the fundus oculi observation device according to the present invention.
Figure 12:
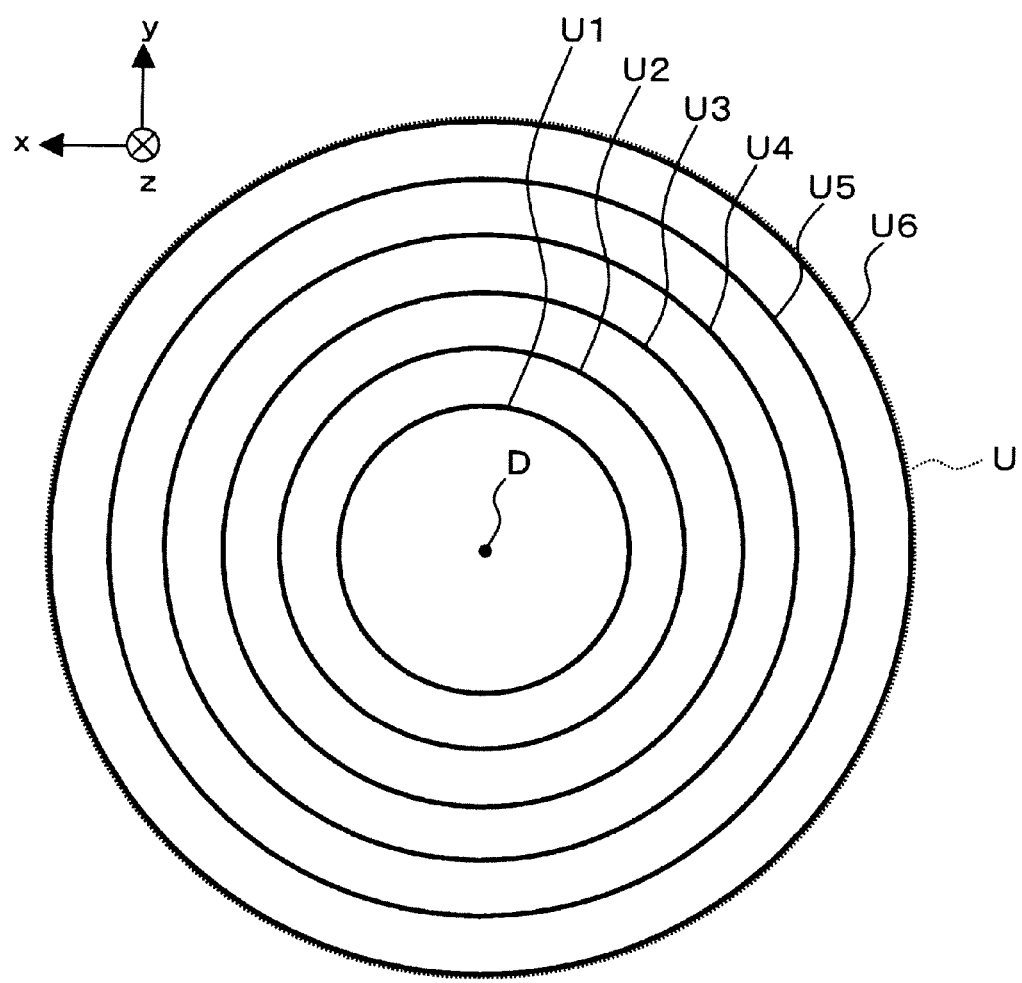
FIG. 12 is a schematic diagram showing an example of a scanning pattern of a signal light in the embodiment of the fundus oculi observation device according to the present invention.
Figure 13:
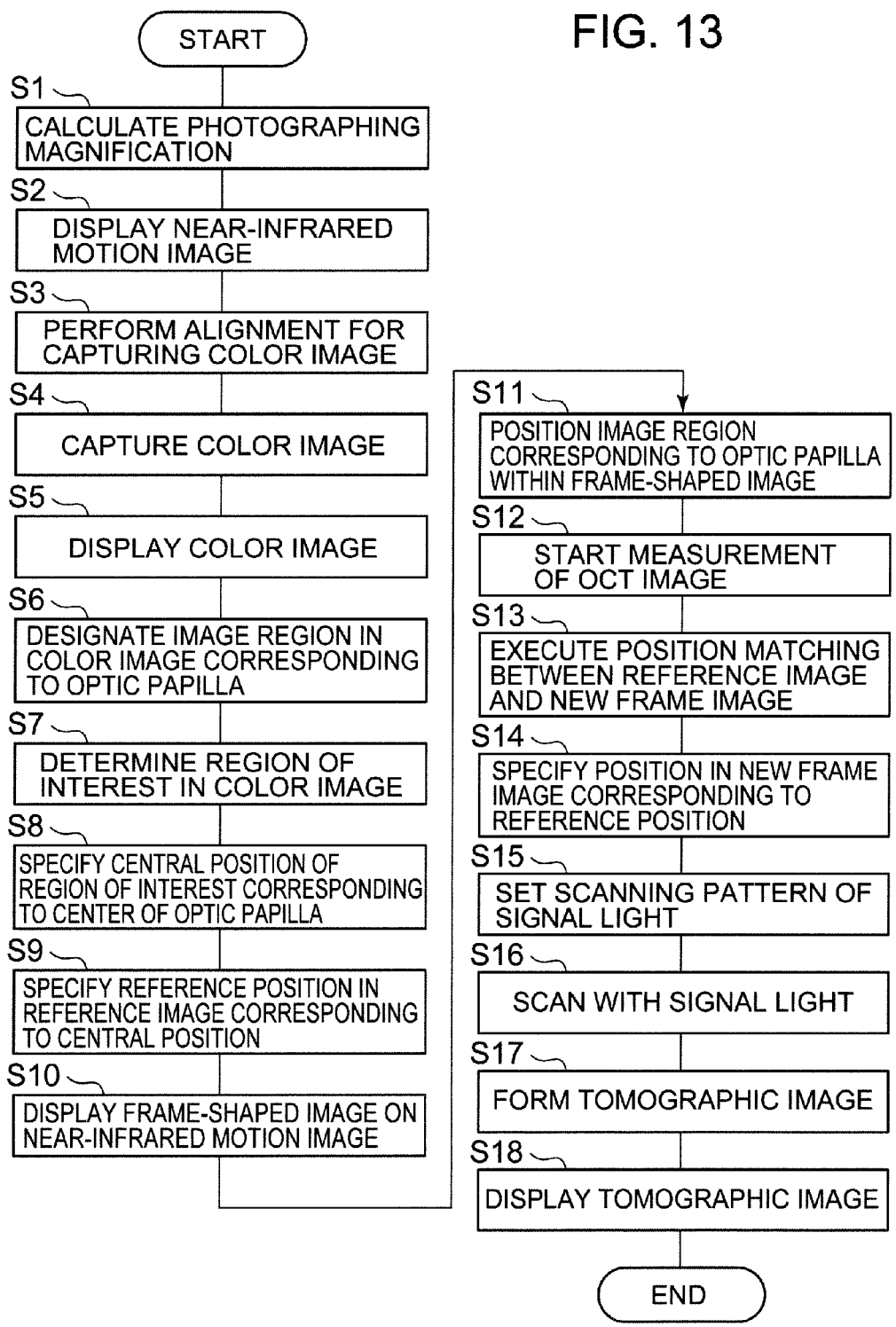
FIG. 13 is a flowchart showing an example of a usage pattern in the embodiment of the fundus oculi observation device according to the present invention.
Figure 14:
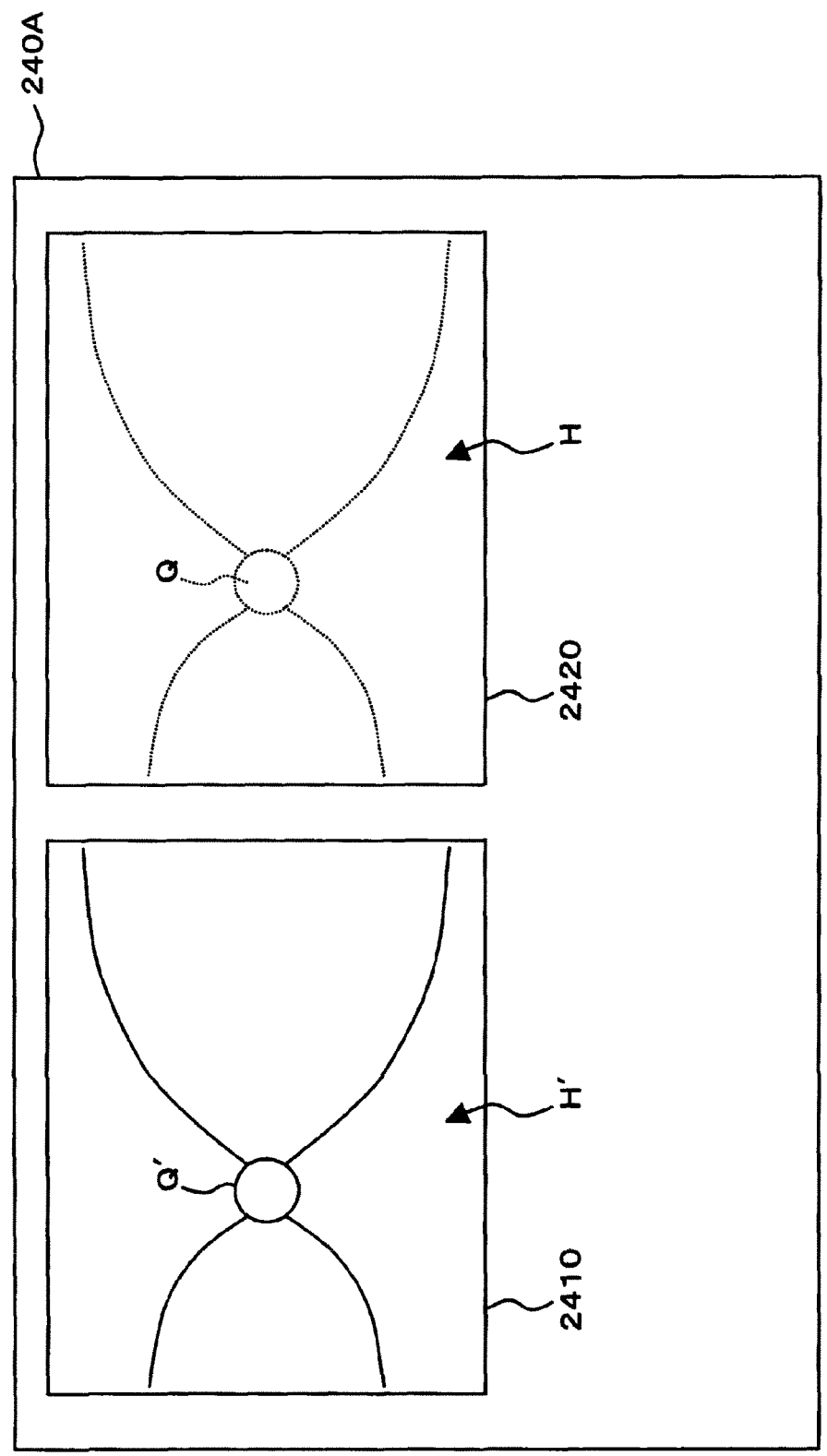
FIG. 14 is a schematic diagram showing an example of a display screen in the usage pattern in the embodiment of the fundus oculi observation device according to the present invention.
Figure 15:
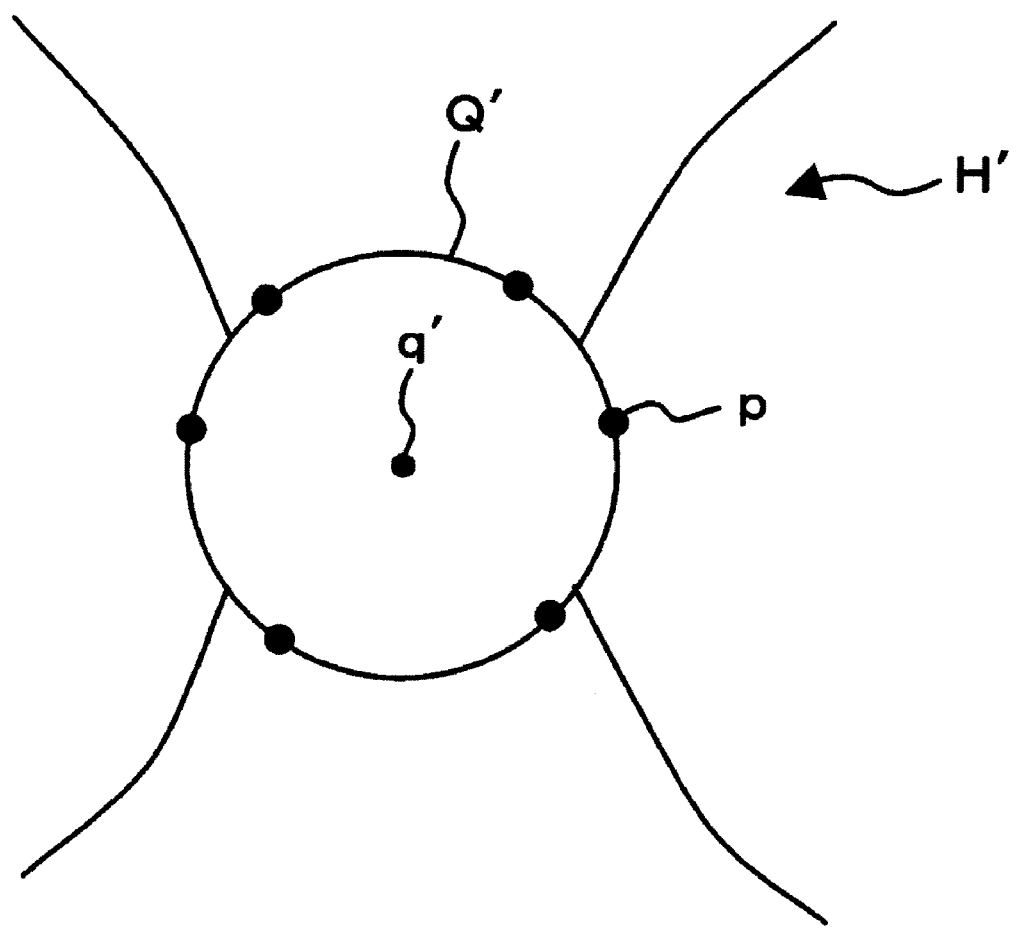
FIG. 15 is a schematic diagram showing an example of a designation pattern of a region of interest in the usage pattern in the embodiment of the fundus oculi observation device according to the present invention.
Figure 16:
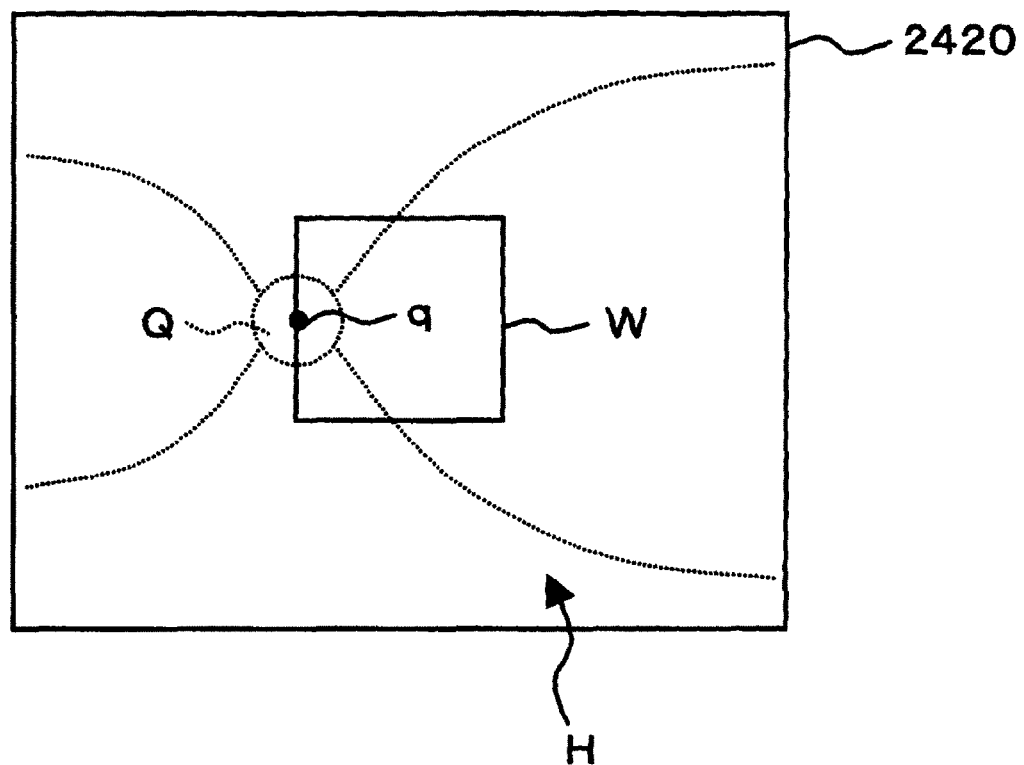
FIG. 16 is a schematic diagram showing an example of a display screen in the usage pattern in the embodiment of the fundus oculi observation device according to the present invention.
Figure 17:
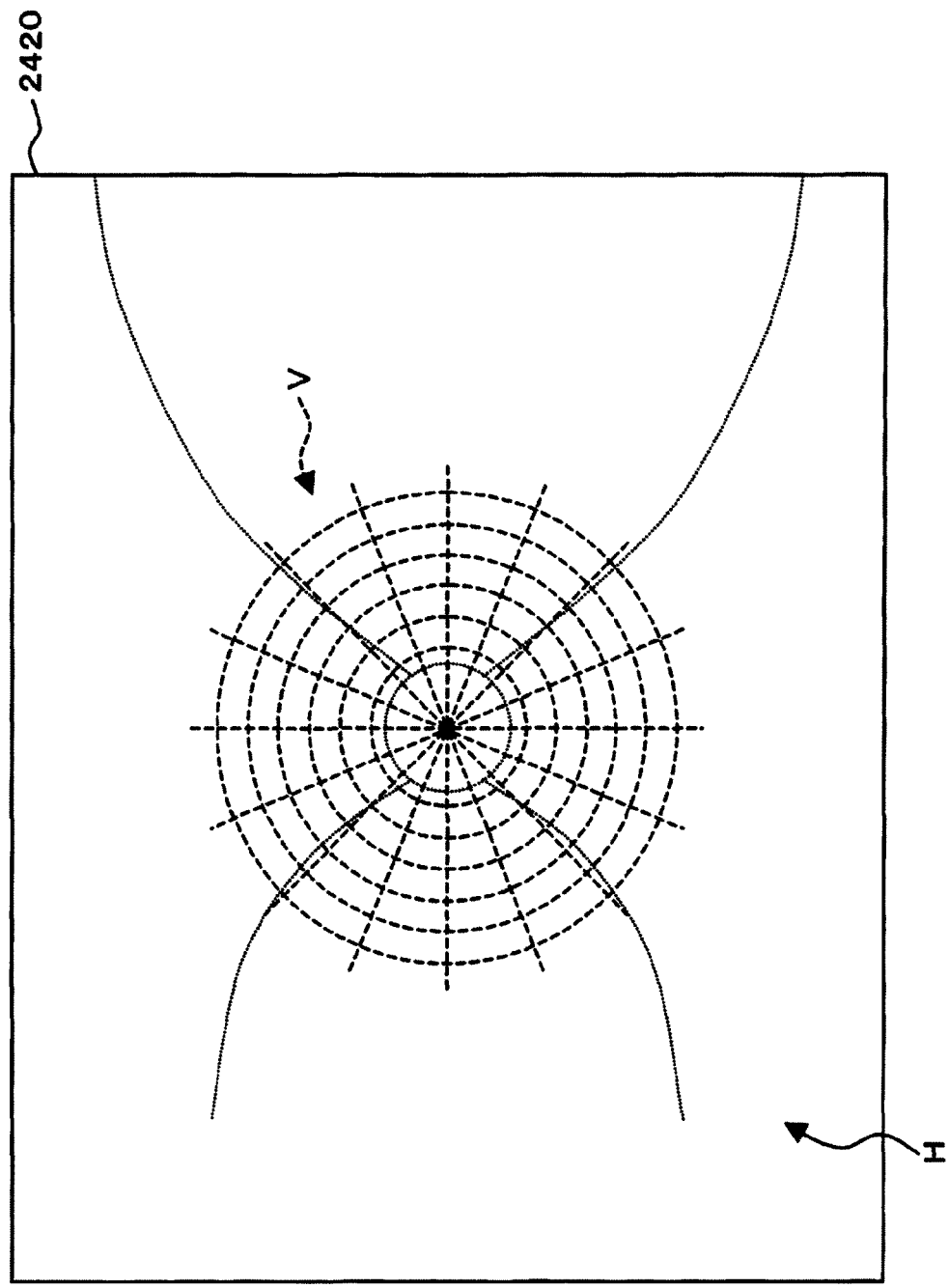
FIG. 17 is a schematic diagram showing an example of a scanning pattern set by the usage pattern in the embodiment of the fundus oculi observation device according to the present invention.
Figure 18:
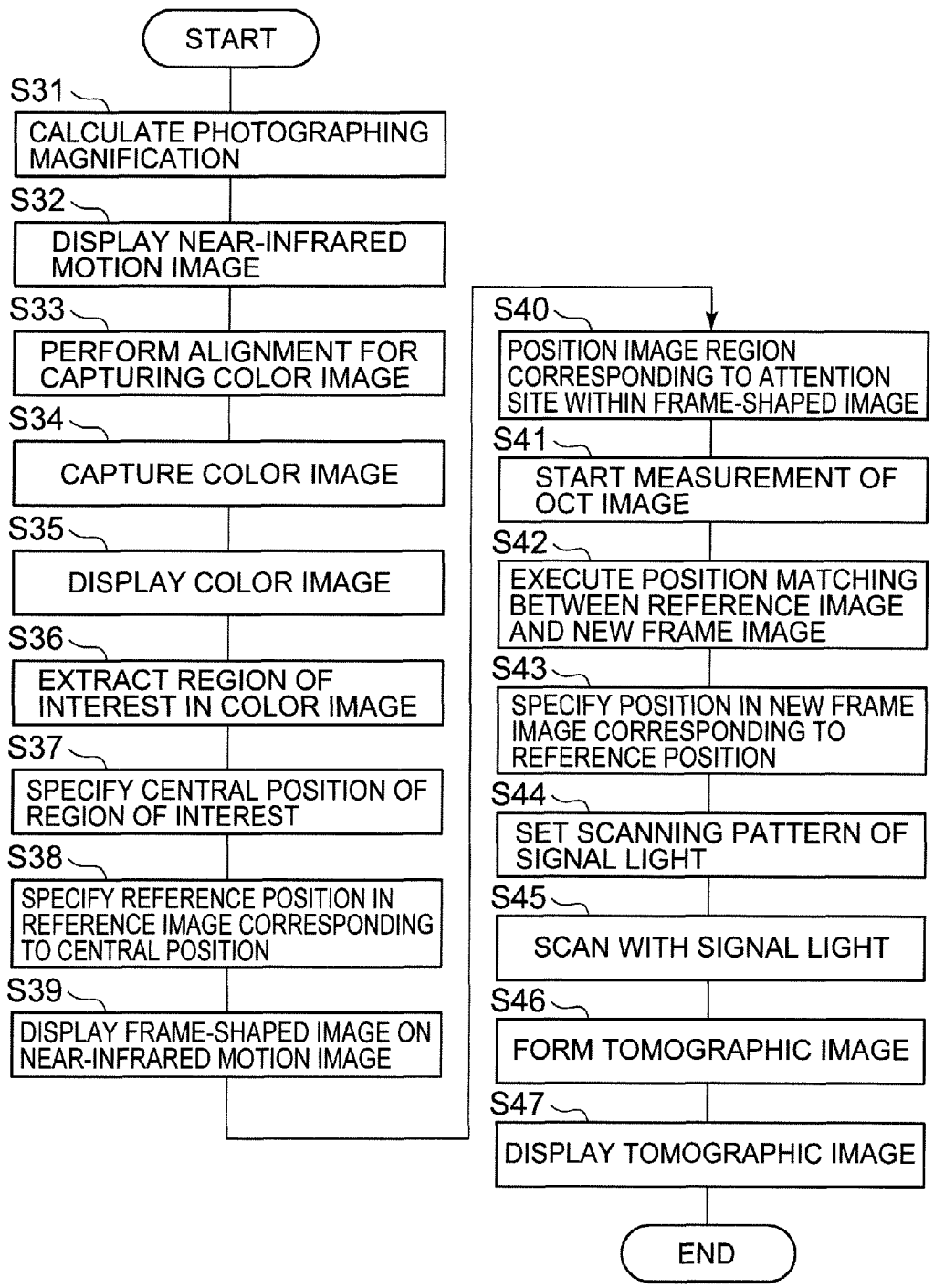
FIG. 18 is a flow chart showing an example of the usage pattern in the embodiment of the fundus oculi observation device according to the present invention.

DESCRIPTION OF REFERENCE NUMERALS AND SYMBOLS 1 fundus oculi observation device
1A retinal camera unit
10, 12 imaging devices
101 observation light source
103 imaging light source
140 LCD
141 scan unit
141A, 141B Galvano mirrors
150 OCT unit
160 low-coherence light source
162 optical coupler
174 reference mirror
180 spectrometer
184 CCD
190 half mirror
190A alignment optical system
190a alignment light source
190d two-hole aperture
200 arithmetic and control unit
204a control program
210 controller
211 main controller
212 storage
213 scan setting part
214 magnification calculator
220 image forming part
230 image processor
231 image analyzer
240 user interface
240A display
240B manipulation part
241, 242 mirror drive mechanisms
E eye
Ef fundus oculi
R, T, U scanning regions
Ri, Ti, Ui scanning lines
Rij scanning points
H near-infrared motion image
H' color image
W frame-shaped image

The invention claimed is:

1. A fundus oculi observation device that has a forming part configured to form a motion image of a fundus oculi, an interference-light generator configured to split a low-coherence light into a signal light and a reference light and superimpose the signal light propagated through the fundus oculi and the reference light propagated through a reference object to generate an interference light, and a detector configured to detect the interference light, and that forms a tomographic image of the fundus oculi based on a result of detection of the interference light, the fundus oculi observation device comprising:

a scanner configured to scan the fundus oculi with the signal light;
a storage configured to store a still image of the fundus oculi;
a specifying part configured to, when a motion image is being formed by the forming part, specify an image region in the motion image corresponding to a region of interest in the still image;
a scan setting part configured to set a scan region including the image region in the motion image; and
a controller configured to control the scanner to scan with the signal light within the scan region based on the image region, and
the fundus oculi observation device forming a tomographic image based on a result of detection of an interference light based on the scan signal light.

2. The fundus oculi observation device according to claim 1, wherein:
the forming part is configured to form the motion image by successively forming frame images of the fundus oculi at a predetermined time interval;
the specifying part is configured to specify an image region in one frame image corresponding to the region of interest in the still image and specify an image region in another frame image corresponding to the image region in the one frame image; and
the controller is configured to scan with the signal light based on the image region in the other frame image.

3. The fundus oculi observation device according to claim 1, wherein the specifying part is configured to, for one frame image of a motion image formed by the forming part, specify an image region corresponding to the region of interest in the still image and, for each frame image formed later than the one frame image, specify an image region corresponding to the image region in the one frame image.

4. The fundus oculi observation device according to claim 1, wherein the specifying part includes an image display configured to display the still image and the motion image and a designating part for designating a region of interest in the displayed still image, and is configured to specify an image region in the motion image corresponding to the designated region of interest.

5. The fundus oculi observation device according to claim 4, wherein:
the region of interest has a predetermined shape;
the specifying part is configured to obtain a characteristic position in the region of interest according to the predetermined shape and obtain a position in the motion image corresponding to the characteristic position; and
the controller is configured to control to scan with the signal light so as to pass through a position in the fundus oculi corresponding to the obtained position.

6. The fundus oculi observation device according to claim 5, wherein:
the predetermined shape is a substantially circular shape;
the specifying part is configured to obtain a central position in the designated region of interest as the characteristic position and obtain a position in the motion image corresponding to the central position; and
the controller is configured to control to scan with the signal light along a plurality of scanning lines arranged radially around a position in the fundus oculi corresponding to the position in the motion image.

7. The fundus oculi observation device according to claim 5, wherein:
the predetermined shape is a substantially circular shape;
the specifying part is configured to obtain a central position in the designated region of interest as the characteristic position and obtain a position in the motion image corresponding to the central position; and the controller is configured to control to scan with the signal light along one or more circular scanning lines arranged around a position in the fundus oculi corresponding to the position in the motion image.

8. The fundus oculi observation device according to claim 6, wherein the controller is configured to control to scan with the signal light along one or more circular scanning lines arranged around a position in the fundus oculi corresponding to the position in the motion image.

9. The fundus oculi observation device according to claim 1, wherein the specifying part includes an extracting part configured to analyze the still image based on preset pixel value information and extract a region of interest, and is configured to specify an image region in the motion image corresponding to the extracted region of interest.

10. The fundus oculi observation device according to claim 1, further comprising:
   a fixation target projecting part configured to project a fixation target to the fundus oculi;
   a display configured to display the motion image; and
   an manipulation part,
   wherein the controller is configured to control to display a frame-shaped image of a preset size on the motion image and change a projection position of the fixation target to the fundus oculi in response to an operation from the manipulation part, and
   wherein the projection position of the fixation target can be changed so that a region of interest in the motion image is placed in the frame-shaped image.

11. The fundus oculi observation device according to claim 1, further comprising an alignment target projecting part configured to project, to the fundus oculi, an alignment target for adjusting a position of a device optical system with respect to an eye.

12. The fundus oculi observation device according to claim 1, wherein the controller is configured to calculate a magnification of an ocular optical system of an eye and control to scan with the signal light based on the image region and the magnification.

13. The fundus oculi observation device according to claim 1, wherein:
   the forming part is configured to capture a motion image of a surface of the fundus oculi by using an illumination light of near-infrared region; and
   the still image is a color image of the surface of the fundus oculi captured by using an illumination light of visible region, or a fluorescent image of the surface of the fundus oculi captured by administering a fluorescent agent to a subject.

14. The fundus oculi observation device according to claim 1, wherein:
   the forming part is configured to form a tomographic motion image of the fundus oculi; and
   the still image is a tomographic still image of the fundus oculi.

15. The fundus oculi observation device according to claim 1, wherein:
   the forming part is configured to form a still image of the fundus oculi while forming a motion image of the fundus oculi; and
   the specifying part is configured to specify an image region in the motion image corresponding to a region of interest in the still image.

* * * * *